(12) United States Patent
Dahme et al.

(10) Patent No.: US 10,373,598 B2
(45) Date of Patent: Aug. 6, 2019

(54) INTEGRATED ACOUSTIC EMISSION TRANSDUCER APPARATUS AND METHODS

(71) Applicant: Fisher Controls International LLC, Marshalltown, IA (US)

(72) Inventors: Bret Anthony Dahme, Marshalltown, IA (US); Shawn Anderson, Haverhill, IA (US)

(73) Assignee: Fisher Controls International LLC, Marshalltown, IA (US)

( * ) Notice: Subject to any disclaimer, the term of this patent is extended or adjusted under 35 U.S.C. 154(b) by 133 days.

(21) Appl. No.: 15/710,244

(22) Filed: Sep. 20, 2017

(65) Prior Publication Data

US 2019/0088240 A1 Mar. 21, 2019

(51) Int. Cl.
*G01N 29/14* (2006.01)
*G01H 11/08* (2006.01)
(Continued)

(52) U.S. Cl.
CPC .............. *G10K 11/02* (2013.01); *G01H 1/00* (2013.01); *G01H 11/08* (2013.01); *G01N 29/14* (2013.01); *G01N 2291/02836* (2013.01)

(58) Field of Classification Search
CPC .......... G10K 11/02; G01H 1/00; G01H 11/08; G01N 29/14; G01N 2291/02836; G01N 29/42; G01N 29/449; G01N 2291/0258; G01M 13/003; G01M 13/028; G01M 13/045; H04R 3/04
(Continued)

(56) References Cited

U.S. PATENT DOCUMENTS

| | | | |
|---|---|---|---|
| 4,201,092 A | 5/1980 | Dau | |
| 4,327,576 A * | 5/1982 | Dickey | G01M 3/243 73/40.5 A |

(Continued)

FOREIGN PATENT DOCUMENTS

| | | |
|---|---|---|
| EP | 0288979 | 11/1988 |
| EP | 2623949 | 8/2013 |

(Continued)

OTHER PUBLICATIONS

Billmann et al., "Leak Detection methods for Pipelines," Automatica, vol. 23, No. 3, 1987, 5 pages.

(Continued)

*Primary Examiner* — Lisa M Caputo
*Assistant Examiner* — Rose M Miller
(74) *Attorney, Agent, or Firm* — Hanley, Flight & Zimmerman, LLC

(57) ABSTRACT

Integrated acoustic emission transducer apparatus and methods are described. An example apparatus includes an acoustic emission sensor having a data extractor and a process variable determiner integrated within the acoustic emission sensor. The acoustic emission sensor is to generate an acoustic emission signal. The data extractor is to extract signal data from the acoustic emission signal. The process variable determiner is to determine process variable data based on the extracted signal data. The process variable data includes at least one of leakage rate data, flow rate data, flow capacity data, flow area data, flow velocity data, mass accumulation data, or volume accumulation data.

20 Claims, 8 Drawing Sheets

(51) Int. Cl.
*G01H 1/00* (2006.01)
*G10K 11/02* (2006.01)
*G01K 11/02* (2006.01)

(58) Field of Classification Search
USPC .............................................. 73/587, 40.5 A
See application file for complete search history.

(56) References Cited

U.S. PATENT DOCUMENTS

| | | | |
|---|---|---|---|
| 4,609,994 | A | 9/1986 | Bassim et al. |
| 4,768,380 | A | 9/1988 | Vermeiren et al. |
| 5,142,916 | A | 9/1992 | Yamaguchi |
| 5,679,900 | A | 10/1997 | Smulders |
| 2007/0182581 | A1 | 8/2007 | Elwell |
| 2010/0139403 | A1 | 6/2010 | Liang et al. |
| 2014/0182381 | A1 | 7/2014 | Comeaux et al. |
| 2015/0377667 | A1* | 12/2015 | Ahmad ............... G01N 29/14 702/48 |
| 2016/0011072 | A1* | 1/2016 | Hale ................... G01M 3/24 702/48 |
| 2016/0369624 | A1 | 12/2016 | Ahmad et al. |
| 2017/0131240 | A1 | 5/2017 | Aura et al. |
| 2018/0341248 | A1* | 11/2018 | Mehr ................ G05B 19/4099 |
| 2019/0086366 | A1 | 3/2019 | Dahme |

FOREIGN PATENT DOCUMENTS

| | | |
|---|---|---|
| JP | S61182574 | 8/1986 |
| JP | H07120440 | 5/1995 |

OTHER PUBLICATIONS

Dimmick et al., "Acoustical Valve Leak Dectector for Fluid System Maintenance," Naval Engineers Journal, Apr. 1979, 13 pages.

Kupperman et al., "Acoustic Leak Detection for Reactor Coolant Systems," Nuclear Engineering and Design 86 (1985) 1-20, 8 pages.

International Searching Authority, "International Search Report," issued in connection with International Patent Application No. PCT/US2018/048121, dated Nov. 20, 2018, 6 pages.

International Searching Authority, "Written Opinion," issued in connection with International Patent Application No. PCT/US2018/048121, dated Nov. 20, 2018, 9 pages.

International Searching Authority, "International Search Report," issued in connection with International Patent Application No. PCT/US2018/050320, dated Dec. 20, 2018, 6 pages.

International Searching Authority, "Written Opinion," issued in connection with International Patent Application No. PCT/US2018/050320, dated Dec. 20, 2018, 6 pages.

United States Patent and Trademark Office, "Non-Final Office Action," issued in connection with U.S. Appl. No. 15/710,270, dated Apr. 1, 2019, 15 pages.

* cited by examiner

US 10,373,598 B2

INTEGRATED ACOUSTIC EMISSION TRANSDUCER APPARATUS AND METHODS

FIELD OF THE DISCLOSURE

This disclosure relates generally to acoustic emission apparatus and methods and, more specifically, to integrated acoustic emission transducer apparatus and methods.

BACKGROUND

Acoustic emission sensors generate acoustic emission signals (e.g., an electrical voltage signal) in response to acoustic emissions (e.g., transient elastic waves) sensed, measured and/or detected via a sensing element (e.g., one or more piezoelectric crystals) of the acoustic emission sensor. Sources of acoustic emissions may include the formation and/or propagation of a material defect (e.g., a crack), slip and/or dislocation movements of a material, etc.

Conventional acoustic emission measurement and detection environments include an acoustic emission sensor, a preamplifier, a filter, an amplifier, an analog to digital converter, and a data processing device (e.g., a computer). In such conventional environments, the acoustic emission signals are typically conditioned and/or modified via the preamplifier, the filter, the amplifier, and the analog to digital converter, and then subsequently analyzed at the data processing device to detect and/or characterize acoustic emission events (e.g., formation and/or propagation of a material defect, determination of a leakage rate, etc.) associated with the acoustic emission signals.

SUMMARY

Integrated acoustic emission transducer apparatus and methods are disclosed herein. In some disclosed examples, an apparatus comprises an acoustic emission sensor including a data extractor and a process variable determiner. In some disclosed examples, the acoustic emission sensor is to generate an acoustic emission signal. In some disclosed examples, the data extractor is to extract signal data from the acoustic emission signal. In some disclosed examples, the process variable determiner is to determine process variable data based on the extracted signal data. In some disclosed examples, the process variable data includes at least one of leakage rate data, flow rate data, flow capacity data, flow area data, flow velocity data, mass accumulation data, or volume accumulation data.

In some disclosed examples, a method comprises extracting signal data at an acoustic emission sensor from an acoustic emission signal generated via the acoustic emission sensor. In some disclosed examples, the method further comprises determining process variable data at the acoustic emission sensor based on the extracted signal data. In some disclosed examples, the process variable data includes at least one of leakage rate data, flow rate data, flow capacity data, flow area data, flow velocity data, mass accumulation data, or volume accumulation data.

In some examples, a non-transitory computer readable storage medium comprising instructions is disclosed. In some disclosed examples, the instructions, when executed, cause a processor to extract signal data at an acoustic emission sensor from an acoustic emission signal generated via the acoustic emission sensor. In some disclosed examples, the instructions, when executed, further cause the processor to determine process variable data at the acoustic emission sensor based on the extracted signal data. In some disclosed examples, the process variable data includes at least one of leakage rate data, flow rate data, flow capacity data, flow area data, flow velocity data, mass accumulation data, or volume accumulation data.

In some disclosed examples, an apparatus comprises an external preamplifier device including a data extractor and a process variable determiner. In some disclosed examples, the external preamplifier device is to receive an acoustic emission signal generated via an acoustic emission sensor operatively coupled to the external preamplifier device. In some disclosed examples, the data extractor is to extract signal data from the acoustic emission signal. In some disclosed examples, the process variable determiner is to determine process variable data based on the extracted signal data. In some disclosed examples, the process variable data includes at least one of leakage rate data, flow rate data, flow capacity data, flow area data, flow velocity data, mass accumulation data, or volume accumulation data.

In some disclosed examples, a method comprises extracting signal data at an external preamplifier device from an acoustic emission signal received at the external preamplifier device. In some disclosed examples, the acoustic emission signal is generated via an acoustic emission sensor operatively coupled to the external preamplifier device. In some disclosed examples, the method further comprises determining process variable data at the external preamplifier device based on the extracted signal data. In some disclosed examples, the process variable data includes at least one of leakage rate data, flow rate data, flow capacity data, flow area data, flow velocity data, mass accumulation data, or volume accumulation data.

In some examples, a non-transitory computer readable storage medium comprising instructions is disclosed. In some disclosed examples, the instructions, when executed, cause a processor to extract signal data at an external preamplifier device from an acoustic emission signal received at the external preamplifier device. In some disclosed examples, the acoustic emission signal is generated via an acoustic emission sensor operatively coupled to the external preamplifier device. In some disclosed examples, the instructions, when executed, further cause the processor to determine process variable data at the external preamplifier device based on the extracted signal data. In some disclosed examples, the process variable data includes at least one of leakage rate data, flow rate data, flow capacity data, flow area data, flow velocity data, mass accumulation data, or volume accumulation data.

Figure 1:
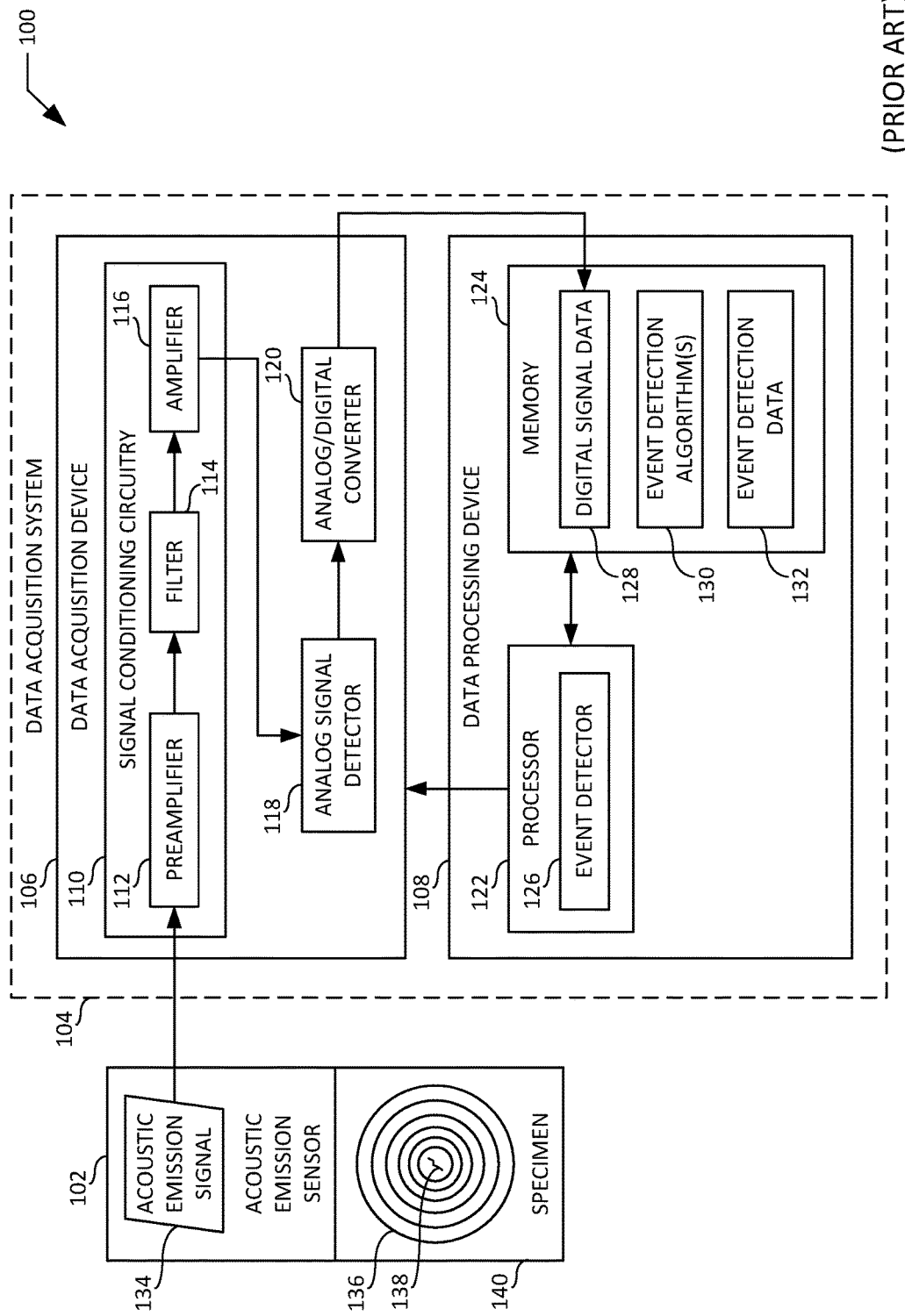
FIG. 1 is a block diagram of a known acoustic emission measurement and detection environment.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness.

DETAILED DESCRIPTION

Conventional acoustic emission measurement and detection environments include an acoustic emission sensor, a preamplifier, a filter, an amplifier, an analog to digital converter, and a data processing device (e.g., a computer). In such conventional environments, the acoustic emission signals are typically conditioned and/or modified via the preamplifier, the filter, the amplifier, and the analog to digital converter, and then subsequently analyzed at the data processing device to detect and/or characterize acoustic emission events (e.g., formation and/or propagation of a material defect, determination of a leakage rate, etc.) associated with the acoustic emission signals.

In some known acoustic emission measurement and detection environments, signal conditioning circuitry including the preamplifier, the filter, and the amplifier is included within a data acquisition device that also includes the analog to digital converter. In other known acoustic emission measurement and detection environments, the preamplifier and the filter of the signal conditioning circuitry are integrated within the acoustic emission sensor, rather than being integrated within the data acquisition device. In still other known acoustic emission measurement and detection environments, the preamplifier and the filter of the signal conditioning circuitry are integrated within an external preamplifier device operatively located and/or positioned between the acoustic emission sensor and the data acquisition device, rather than being integrated within the data acquisition device.

The above-described conventional acoustic emission measurement and detection environments require high speed sampling (e.g., via the data acquisition device) and extensive post-processing (e.g., via the data processing device) to produce useful information regarding the integrity and/or health of the material(s) (e.g., process equipment) being monitored and/or evaluated. Examples of such useful information may include determinations and/or estimations of leakage rate, flow rate, flow capacity, flow area, flow velocity, mass accumulation, and/or volume accumulation associated with a process occurring within process equipment being monitored by the acoustic emission sensor, and may further include determinations and/or estimations of valve health, valve wear, seal health, seal wear, and/or fugitive emissions associated with the monitored process equipment.

The above-described conventional acoustic emission measurement and detection environments fail to produce useful information (e.g., leakage rate data, flow rate data, valve health data, valve wear data, etc.) in real time. Moreover, the aforementioned high speed sampling and extensive post-processing requirements of such conventional acoustic emission measurement and detections systems necessitate the implementation of high end data acquisition and data processing equipment, which increases the complexity and the cost of the acoustic emission measurement and detection system. The implementation of such high end equipment becomes technologically challenging in low power and/or hazardous environments.

Unlike the above-described conventional acoustic emission measurement and detection environments, the integrated acoustic emission transducer apparatus and methods disclosed herein transduce, convert, and/or restate one or more acoustic emission signal(s) generated by and/or received at the integrated acoustic emission transducer into useful information (e.g., leakage rate, flow rate, valve health, valve wear, etc.) to be presented at the integrated acoustic emission transducer, and/or to be transmitted from the integrated acoustic emission transducer to an external device. Implementing the integrated acoustic emission transducer apparatus and methods disclosed herein advantageously enables one or more acoustic emission signal(s) generated by and/or received at the integrated acoustic emission transducer to be transduced, converted and/or restated into useful information at the integrated acoustic emission transducer in real time without the need for implementing high speed sampling and/or extensive, time-delayed, post-processing of the acoustic emission signal(s) via costly external data acquisition devices and/or external data processing devices. Before describing the details of the disclosed integrated acoustic emission transducer apparatus and methods, a description of a known acoustic emission measurement and detection environment is provided in connection with FIG. 1.

FIG. 1 is a block diagram of a known acoustic emission measurement and detection environment 100. The acoustic emission measurement and detection environment 100 of FIG. 1 includes an acoustic emission sensor 102 and a data acquisition system 104. The data acquisition system 104 of FIG. 1 includes a data acquisition device 106 and a data processing device 108 (e.g., a computer). The data acquisition device 106 includes signal conditioning circuitry 110 implemented as a preamplifier 112, a filter 114, and an amplifier 116. The data acquisition device 106 also includes an analog signal detector 118 and an analog to digital converter 120. The data processing device 108 includes a processor 122 and a memory 124. The processor 122 includes and/or implements an event detector 126. The memory 124 stores digital signal data 128, one or more event detection algorithm(s) 130, and event detection data 132. The processor 122 and/or, more generally, the data processing device 108 of FIG. 1 controls the operation of the data acquisition device 106 of FIG. 1

The acoustic emission sensor 102 of FIG. 1 generates an acoustic emission signal 134 in response to one or more acoustic emission(s) (e.g., transient elastic waves 136 of FIG. 1) sensed, measured and/or detected via a sensing element (not shown) of the acoustic emission sensor 102. The sensing element of the acoustic emission sensor 102 is implemented as one or more piezoelectric crystal(s), as is known in the art. The acoustic emission(s) (e.g., the transient elastic waves 136) are sensed, measured and/or detected by the sensing element of the acoustic emission sensor 102 in response to the formation and/or propagation of a defect (e.g. a crack 138 of FIG. 1) in a specimen 140 of FIG. 1 to which the acoustic emission sensor 102 is coupled. The specimen 140 of FIG. 1 may be an item of process equipment (e.g., a segment of piping and/or conduit, a field device such as a valve, etc.). The acoustic emission signal 134 generated by the acoustic emission sensor 102 is an analog signal. The generated acoustic emission signal 134 is transmitted to and/or received at the data acquisition system 104 of FIG. 1. More specifically, the acoustic emission signal 134 is transmitted to and/or received at the preamplifier 112 of the signal conditioning circuitry 110 of the data acquisition device 106 of the data acquisition system 104 of FIG. 1.

The signal conditioning circuitry 110 of the data acquisition device 106 of FIG. 1 conditions, alters and/or otherwise prepares the generated acoustic emission signal 134 for further processing. The preamplifier 112 of the signal conditioning circuitry 110 of FIG. 1 amplifies, boosts and/or strengthens the generated acoustic emission signal 134. The amplified acoustic emission signal is transmitted from the preamplifier 112 to the filter 114 of the signal conditioning circuitry 110 of FIG. 1. The filter 114 filters the amplified acoustic emission signal based on a non-selectable and/or non-programmable bandwidth associated with the filter 114. The filtered acoustic emission signal is transmitted from the filter 114 to the amplifier 116 of the signal conditioning circuitry 110 of FIG. 1. The amplifier 116 further amplifies, boosts and/or strengthens the filtered acoustic emission signal. The amplified acoustic emission signal is transmitted from the amplifier 116 to the analog signal detector 118 of the data acquisition device 106 of FIG. 1.

Figure 2:
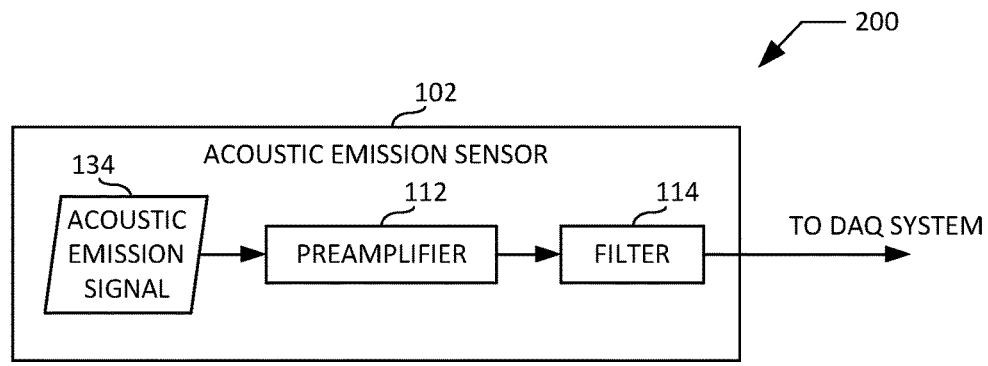
FIG. 2 is a block diagram of a known implementation of the acoustic emission sensor of FIG. 1 modified to include the preamplifier and the filter of FIG. 1.
Figure 3:
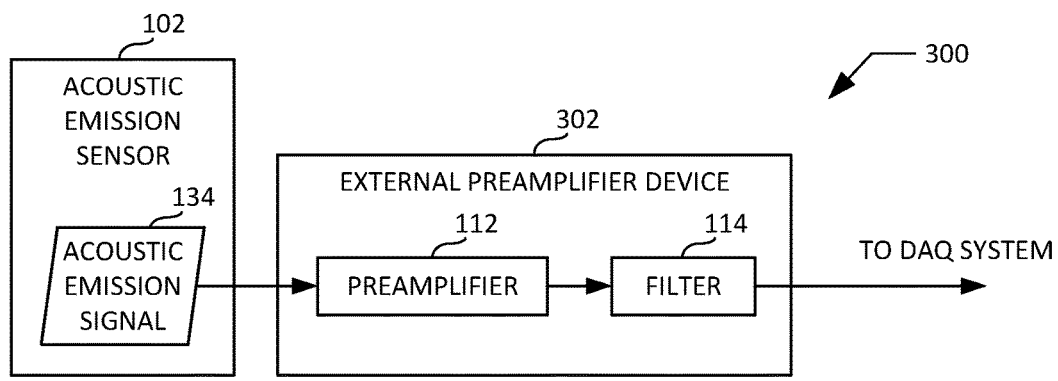
FIG. 3 is a block diagram of a known implementation of an external preamplifier device operatively coupled to the acoustic emission sensor of FIG. 1.

In some known alternative implementations, the preamplifier 112, the filter 114, and/or the amplifier 116 of the signal conditioning circuitry 110 is/are located at (e.g., integrated within) the acoustic emission sensor 102 of FIG. 1, and/or at an external preamplifier device operatively located and/or positioned between the acoustic emission sensor 102 of FIG. 1 and the data acquisition system 104 of FIG. 1. For example, FIG. 2 is a block diagram of a known implementation 200 of the acoustic emission sensor 102 of FIG. 1 modified to include the preamplifier 112 and the filter 114 of FIG. 1. In the example of FIG. 2, the above-described operations and/or functions of the preamplifier 112 and the filter 114 of FIG. 1 are performed at the acoustic emission sensor 102 of FIG. 2, as opposed to being performed at the data acquisition device 106 of the data acquisition system 104 of FIG. 1. As another example, FIG. 3 is a block diagram of a known implementation 300 of an external preamplifier device 302 operatively located and/or positioned between the acoustic emission sensor 102 of FIG. 1 and the data acquisition system 104 of FIG. 1. In the example of FIG. 3, the above-described operations and/or functions of the preamplifier 112 and the filter 114 of FIG. 1 are performed at the external preamplifier device 302 of FIG. 3, as opposed to being performed at the data acquisition device 106 of the data acquisition system 104 of FIG. 1.

Returning to the known acoustic emission measurement and detection environment 100 of FIG. 1, the analog signal detector 118 of the data acquisition device 106 detects the amplified signal transmitted from the amplifier 116 of the signal conditioning circuitry 110 as an analog waveform. The analog to digital converter 120 of the data acquisition device 106 converts the detected analog waveform into the digital signal data 128. The digital signal data 128 is transmitted from the analog to digital converter 120 to the memory 124 of the data processing device 108 of FIG. 1 where the digital signal data 128 is stored for further processing via the processor 122 of the data processing device 108 of FIG. 1.

The processor 122 of the data processing device 108 of FIG. 1 implements the event detector 126 to detect the formation and/or propagation of one or more defect(s) (e.g., the crack 138 of FIG. 1) in the specimen 140 of FIG. 1. The event detector 126 detects one or more event(s) associated with the defect(s) (e.g., a leakage rate associated with the formation and/or propagation of the defect) based on the one or more event detection algorithm(s) 130 stored in the memory 124 and accessible to the processor 122 and/or the event detector 126. The event detector 126 and/or, more generally, the processor 122 of the data processing device 108 of FIG. 1 transmits the event detection data 132 (e.g., data corresponding to one or more event(s) detected by the event detector 126) to the memory 124 of the data processing device 108 where the event detection data 132 is stored for further analysis and/or processing by the processor 122.

Figure 4:
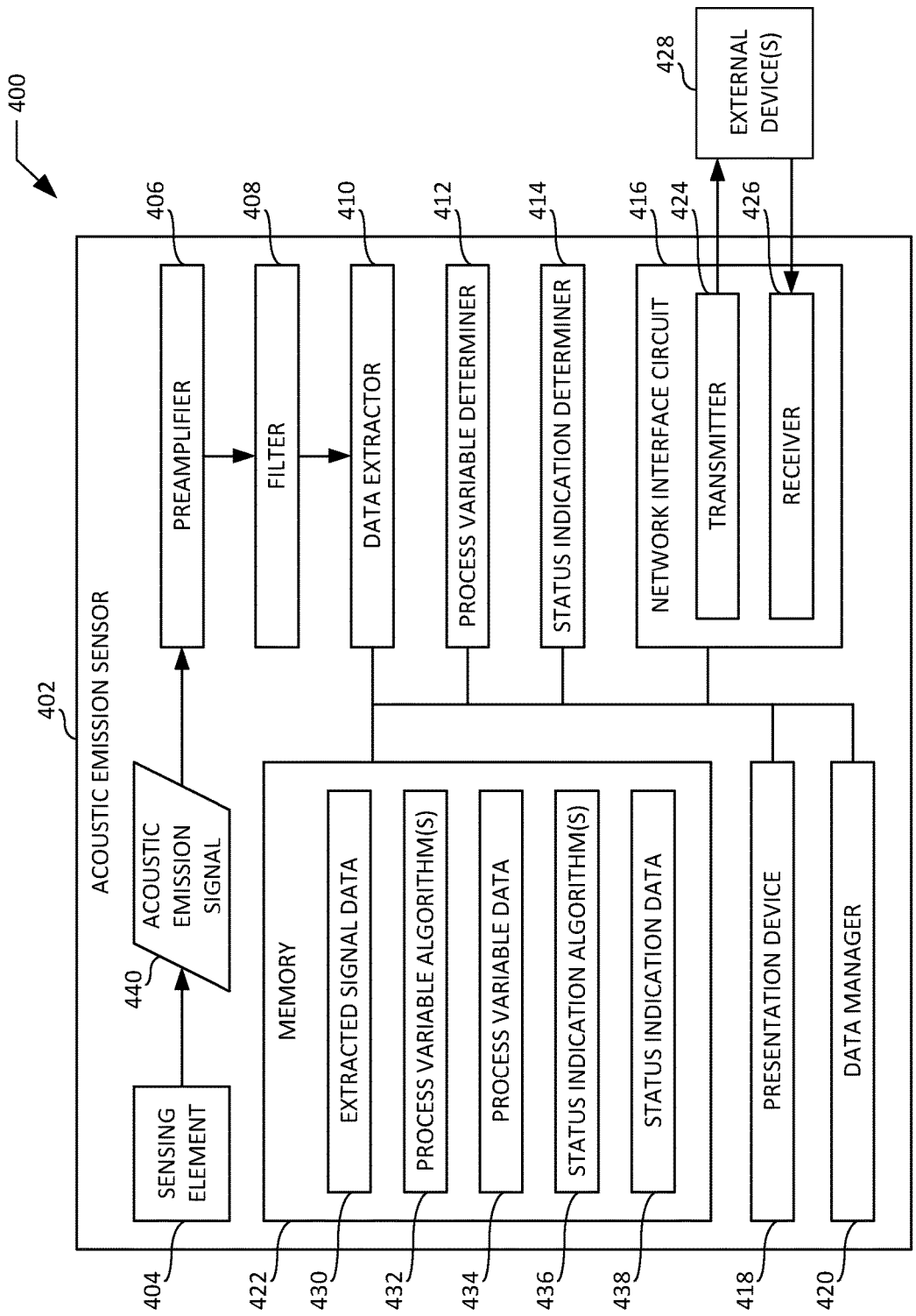
FIG. 4 is a block diagram of a first example integrated acoustic emission transducer implemented via an example acoustic emission sensor constructed in accordance with the teachings of this disclosure.

FIG. 4 is a block diagram of a first example integrated acoustic emission transducer 400 implemented via an example acoustic emission sensor 402 constructed in accordance with the teachings of this disclosure. In the illustrated example of FIG. 4, the acoustic emission sensor 402 includes an example sensing element 404, an example preamplifier 406, an example filter 408, an example data extractor 410, an example process variable determiner 412, an example status indication determiner 414, an example network interface circuit 416, an example presentation device 418, an example data manager 420, and an example memory 422. The network interface circuit 416 of FIG. 4 includes an example transmitter 424 and an example receiver 426 respectively capable of communicating with one or more example external device(s) 428 (e.g., a data processing device, such as a computer). The memory 422 of FIG. 4 stores example extracted signal data 430, one or more example process variable algorithm(s) 432, example process variable data 434, one or more example status indication algorithm(s) 436, and example status indication data 438.

In the illustrated example of FIG. 4, the sensing element 404, the preamplifier 406, the filter 408, the data extractor 410, the process variable determiner 412, the status indication determiner 414, the network interface circuit 416, the presentation device 418, the data manager 420, and the memory 422 are integrated within the acoustic emission sensor 402 of the integrated acoustic emission transducer 400. In other examples, one or more of the filter 408, the data extractor 410, the process variable determiner 412, the status indication determiner 414, the network interface circuit 416, the presentation device 418, the data manager 420, and/or the memory 422 may be integrated within the preamplifier 406 of the acoustic emission sensor 402 of FIG. 4.

The acoustic emission sensor 402 of FIG. 4 generates an example acoustic emission signal 440 in response to one or more acoustic emission(s) (e.g., transient elastic waves) sensed, measured and/or detected via the sensing element 404 of the acoustic emission sensor 402. In some examples, the sensing element 404 of the acoustic emission sensor 402 may be implemented as one or more piezoelectric crystal(s). In some examples, the acoustic emission signal 440 generated by the acoustic emission sensor 402 is an analog signal. In the illustrated example of FIG. 4, the acoustic emission signal 440 generated by the acoustic emission sensor 402 of FIG. 4 is transmitted to and/or received at the preamplifier 406 of the acoustic emission sensor 402 of FIG. 4.

The preamplifier 406 of FIG. 4 amplifies, boosts and/or strengthens the acoustic emission signal 440. In the illustrated example of FIG. 4, the preamplifier 406 amplifies, boosts and/or strengthens the acoustic emission signal 440 prior to the acoustic emission signal 440 being transmitted to and/or received at the filter 408 of the acoustic emission sensor 402 of FIG. 4. In other examples, the preamplifier 406 of FIG. 4 may amplify, boost and/or strengthen the acoustic emission signal 440 after the acoustic emission signal 440 is filtered by the filter 408 of the acoustic emission sensor 402 of FIG. 4. In the illustrated example of FIG. 4, the amplified acoustic emission signal generated by the preamplifier 406 is transmitted to and/or received at the filter 408 of the acoustic emission sensor 402 of FIG. 4.

The filter 408 of FIG. 4 filters the acoustic emission signal 440. The filter 408 of FIG. 4 may be implemented as any type of filter including, for example, active, passive, superheterodyne, envelope detection, capacitor switching, field programmable gate array, finite impulse response, infinite impulse response, etc. In some examples, the filter 408 of FIG. 4 may be implemented as a bandwidth-selectable filter as disclosed in a U.S. Patent Application entitled "Bandwidth-Selectable Acoustic Emission Apparatus and Methods for Transmitting Time-Averaged Signal Data" (Attorney Docket No. 20040/56-13712), filed on Sep. 20, 2017, the entirety of which is hereby incorporated by reference herein. In the illustrated example of FIG. 4, the conditioned (e.g., amplified and filtered) acoustic emission signal generated by the filter 408 is transmitted to and/or received at the data extractor 410 of the acoustic emission sensor 402 of FIG. 4.

The data extractor 410 of FIG. 4 extracts signal data (e.g., the extracted signal data 430 of FIG. 4) from the conditioned acoustic emission signal. In some examples, the extracted signal data 430 of FIG. 4 includes root mean square data associated with the conditioned acoustic emission signal. For example, the data extractor 410 may extract and/or calculate root mean square data from the conditioned acoustic emission signal by squaring the values of the conditioned acoustic emission signal (e.g., squaring the function that defines the waveform of the conditioned acoustic emission signal), by taking the average of the squared values (e.g., the average of the squared function), and by taking the square root of the average values (e.g., the square root of the average function). In other examples, the extracted signal data 430 of FIG. 4 includes average signal level data associated with the conditioned acoustic emission signal. For example, the data extractor 410 may additionally or alternatively extract and/or calculate average signal level data from the conditioned acoustic emission signal by taking the average signal values (e.g., the average of the function that defines the waveform of the conditioned acoustic emission signal) as a function of time. In still other examples, the data extractor 410 may additionally or alternatively extract spectral content data associated with the acoustic emission signal, and/or transient data associated with the acoustic emission signal. The extracted signal data 430 of FIG. 4 may include such spectral content data and/or transient data.

The data extractor 410 of FIG. 4 transmits the extracted signal data 430 to the memory 422 of the acoustic emission sensor 402 where the extracted signal data 430 is stored for further analysis and/or processing. The extracted signal data 430 stored in the memory 422 of FIG. 4 is accessible to the data extractor 410, the process variable determiner 412, the status indication determiner 414, the network interface circuit 416, the presentation device 418, and/or the data manager 420 of the acoustic emission sensor 402 of FIG. 4.

The process variable determiner 412 of FIG. 4 determines process variable data (e.g., the process variable data 434 of FIG. 4) associated with the acoustic emission signal 440 based on the extracted signal data 430 of FIG. 4. In some examples, the process variable determiner 412 of FIG. 4 determines the process variable data 434 of FIG. 4 by applying one or more of the process variable algorithm(s) 432 stored on the memory 422 to the extracted signal data 430 stored on the memory 422. In such examples, the one or more process variable algorithm(s) 432 and the extracted signal data 430 of FIG. 4 are accessible to the process variable determiner 412 from the memory 422 of FIG. 4.

For example, based on the extracted signal data 430 of FIG. 4 and one or more of the process variable algorithm(s) 432 of FIG. 4, the process variable determiner 412 may determine and/or calculate leakage rate data (e.g., one type of the process variable data 434 of FIG. 4) associated with a process (e.g., a flow of fluid) occurring within process equipment (e.g., process piping, a valve, etc.) being monitored via the acoustic emissions sensor 402 of FIG. 4. In other examples, again based on the extracted signal data 430 and one or more of the process variable algorithm(s) 432, the process variable determiner 412 may additionally or alternatively determine and/or calculate other types of process variable data associated with the process occurring within the process equipment. For example, the process variable data 434 determined and/or calculated by the process variable determiner 412 may additionally or alternatively include flow rate data, flow capacity data, flow area data, flow velocity data, mass accumulation data, and/or volume accumulation data associated with the process occurring within the process equipment being monitored by the acoustic emission sensor 402 of FIG. 4.

The process variable determiner 412 of FIG. 4 transmits the process variable data 434 to the memory 422 of the acoustic emission sensor 402 where the process variable data 434 is stored for further analysis and/or processing. The process variable data 434 stored in the memory 422 of FIG. 4 is accessible to the process variable determiner 412, the status indication determiner 414, the network interface circuit 416, the presentation device 418, and/or the data manager 420 of the acoustic emission sensor 402 of FIG. 4.

The status indication determiner 414 of FIG. 4 determines status indication data (e.g., the status indication data 438 of FIG. 4) associated with the acoustic emission signal 440 based on the process variable data 434 and/or based on the extracted signal data 430 of FIG. 4. In some examples, the status indication determiner 414 of FIG. 4 determines the status indication data 438 of FIG. 4 by applying one or more of the status indication algorithm(s) 436 stored on the memory 422 to the process variable data 434 and/or to the extracted signal data 430 stored on the memory 422. In such examples, the one or status indication algorithm(s) 436, the process variable data 434, and/or the extracted signal data 430 of FIG. 4 are accessible to the status indication determiner 414 from the memory 422 of FIG. 4.

For example, based on the process variable data 434 of FIG. 4 and/or the extracted signal data 430 of FIG. 4, and further based on one or more of the status indication algorithm(s) 436 of FIG. 4, the status indication determiner 414 may determine and/or calculate valve health data (e.g., one type of the status indication data 438 of FIG. 4) associated with process equipment (e.g., process piping, a valve, etc.) and/or a process (e.g., a flow of fluid) occurring within the process equipment, as monitored via the acoustic emissions sensor 402 of FIG. 4. In some examples, the valve health data may be expressed and/or represented as a percentage type of status indication associated with a total possible valve health (e.g., a textual, graphical and/or audible signal and/or message indicating that the valve health is eighty percent (80%) of a total possible valve health). In other examples, the valve health data may be expressed and/or represented as a pass/fail type of status indication (e.g., a textual, graphical and/or audible signal and/or message indicating that the valve health satisfies (e.g., passes) a valve health threshold or does not satisfy (e.g., fails) the valve health threshold).

In other examples, again based on the process variable data 434 of FIG. 4 and/or the extracted signal data 430 of FIG. 4, and further based on one or more of the status indication algorithm(s) 436 of FIG. 4, the status indication determiner 414 may additionally or alternatively determine and/or calculate other types of status indication data associated with the process equipment and/or the process occurring within the process equipment. For example, the status indication data 438 determined and/or calculated by the status indication determiner 414 may additionally or alternatively include valve wear data, seal health data, seal wear data, and/or fugitive emissions data associated with the process equipment and/or the process occurring within the process equipment, as monitored by the acoustic emission sensor 402 of FIG. 4. In such other examples, the different types of status indication data may be expressed and/or represented in any form, including those forms described above in relation to the valve heath data.

The status indication determiner 414 of FIG. 4 transmits the status indication data 438 to the memory 422 of the acoustic emission sensor 402 where the status indication data 438 is stored for further analysis and/or processing. The status indication data 438 stored in the memory 422 of FIG. 4 is accessible to the status indication determiner 414, the network interface circuit 416, the presentation device 418, and/or the data manager 420 of the acoustic emission sensor 402 of FIG. 4.

The network interface circuit 416 of FIG. 4 may be implemented by any type of interface standard, such as an Ethernet interface, a universal serial bus (USB), and/or a PCI express interface. The network interface circuit 416 of the illustrated example includes the transmitter 424 and the receiver 426 of FIG. 4, and may further include a modem and/or a network interface card to facilitate exchange of data with the one or more external device(s) 428 of FIG. 4 via a network. In some examples, the network over which the transmitter 424 and/or the receiver 426 of the network interface circuit 416 of FIG. 4 exchange(s) data with the one or more external device(s) 428 may be facilitated via 4-20 milliamp wiring and/or via one or more communication protocol(s) including, for example, Highway Addressable Remote Transducer (HART), Foundation Fieldbus, Transmission Control Protocol/Internet Protocol (TCP/IP), Profinet, Modbus and/or Ethernet.

The transmitter 424 of the network interface circuit 416 of FIG. 4 transmits data from the acoustic emission sensor 402 of FIG. 4 to one or more of the external device(s) 428 of FIG. 4. For example, the transmitter 424 may transmit some or all of the process variable data 434 of FIG. 4, and/or some or all of the status indication data 438 of FIG. 4 from the acoustic emission sensor 402 to one or more of the external device(s) 428. In some examples, the process variable data 434 and/or the status indication data 438 of FIG. 4 transmitted by the transmitter 424 may be the only data transmitted by the transmitter from the acoustic emission sensor 402 to the one or more external device(s) 428 of FIG. 4. In some examples, the transmission of data via the transmitter 424 of the network interface circuit 416 of the acoustic emission sensor 402 of FIG. 4 is controlled and/or managed by the data manager 420 of FIG. 4, as described below.

The presentation device 418 of FIG. 4 presents data in visual and/or audible form at the acoustic emission sensor 402 of FIG. 4 including, for example, some or all of the process variable data 434 of FIG. 4, and/or some or all of the status indication data 438 of FIG. 4. For example, the presentation device 418 may be implemented as one or more of a light emitting diode, a touchscreen, and/or a liquid crystal display for presenting visual information, and/or a speaker for presenting audible information. In some examples, the presentation of data via the presentation device 418 of the acoustic emission sensor 402 of FIG. 4 is controlled and/or managed by the data manager 420 of FIG. 4, as described below.

The data manager 420 of FIG. 4 controls and/or manages the transmission of data via the transmitter 424 of FIG. 4. For example, the data manager 420 may determine the conditions, circumstances, and/or timing under which the transmitter 424 is to transmit some or all of the process variable data 434 and/or some or all of the status indication data 438 of FIG. 4 from the acoustic emission sensor 402 of FIG. 4 to one or more of the external device(s) 428 of FIG. 4. In some examples, the data manager 420 may instruct and/or otherwise control the transmitter 424 to transmit some or all of the process variable data 434 and/or some or all of the status indication data 438 of FIG. 4 based on one or more control signal(s) communicated between the data manager 420 and the transmitter 424.

The data manager 420 of FIG. 4 also controls and/or manages the presentation of data at the presentation device 418 of the acoustic emission sensor 402 of FIG. 4. For example, the data manager 420 may determine the conditions, circumstances, and/or timing under which the presentation device 418 is to present some or all of the process variable data 434 and/or some or all of the status indication data 438 of FIG. 4. In some examples, the data manager 420 may instruct and/or otherwise control the presentation device 418 to present some or all of the process variable data 434 and/or some or all of the status indication data 438 of FIG. 4 based on one or more control signal(s) communicated between the data manager 420 and the presentation device 418.

The memory 422 of FIG. 4 stores the extracted signal data 430, the one or more process variable algorithm(s) 432, the process variable data 434, the one or more status indication algorithm(s) 436, and the status indication data 438. The memory 422 of FIG. 4 may also store some or all of the data and/or data structures transmitted by the transmitter 424 of FIG. 4 and/or received by the receiver 426 of FIG. 4. The memory 422 of FIG. 4 may be implemented by any type(s) and/or any number(s) of storage device(s) such as a storage drive, a flash memory, a read-only memory (ROM), a random-access memory (RAM), a cache, and/or any other storage medium in which data is stored for any duration (e.g., for extended time periods, permanently, brief instances, for temporarily buffering, and/or for caching of the data). The data stored in the memory 422 of FIG. 4 may be stored in any file and/or data structure format, organization scheme, and/or arrangement. The memory 422 of FIG. 4 is accessible to the data extractor 410, the process variable determiner 412, the status indication determiner 414, the network interface circuit 416 (including the transmitter 424 and the receiver 426), the presentation device 418, the data manager 420, and/or, more generally, the acoustic emission sensor 402 of FIG. 4.

While an example manner of implementing the integrated acoustic emission transducer 400 is illustrated in FIG. 4, one or more of the elements, processes and/or devices illustrated in FIG. 4 may be combined, divided, re-arranged, omitted, eliminated and/or implemented in any other way. Further, the example sensing element 404, the example preamplifier 406, the example filter 408, the example data extractor 410, the example process variable determiner 412, the example status indication determiner 414, the example network interface circuit 416, the example presentation device 418, the example data manager 420, the example memory 422 and/or, more generally the example acoustic emission sensor 402 of the integrated acoustic emission transducer 400 of FIG. 4 may be implemented by hardware, software, firmware and/or any combination of hardware, software and/or firmware. Thus, for example, any of the example sensing element 404, the example preamplifier 406, the example filter 408, the example data extractor 410, the example process variable determiner 412, the example status indication determiner 414, the example network interface circuit 416, the example presentation device 418, the example data manager 420, the example memory 422 and/or, more generally the example acoustic emission sensor 402 of the integrated acoustic emission transducer 400 of FIG. 4 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example sensing element 404, the example preamplifier 406, the example filter 408, the example data extractor 410, the example process variable determiner 412, the example status indication determiner 414, the example network interface circuit 416, the example presentation device 418, the example data manager 420, the example memory 422 and/or, more generally the example acoustic emission sensor 402 of the integrated acoustic emission transducer 400 of FIG. 4 is/are hereby expressly defined to include a non-transitory computer readable storage device or storage disk such as a memory, a digital versatile disk (DVD), a compact disk (CD), a Blu-ray disk, etc. including the software and/or firmware. Further still, the example integrated acoustic emission transducer 400 of FIG. 4 may include one or more elements, processes and/or devices in addition to, or instead of, those illustrated in FIG. 4, and/or may include more than one of any or all of the illustrated elements, processes and devices.

Figure 5:
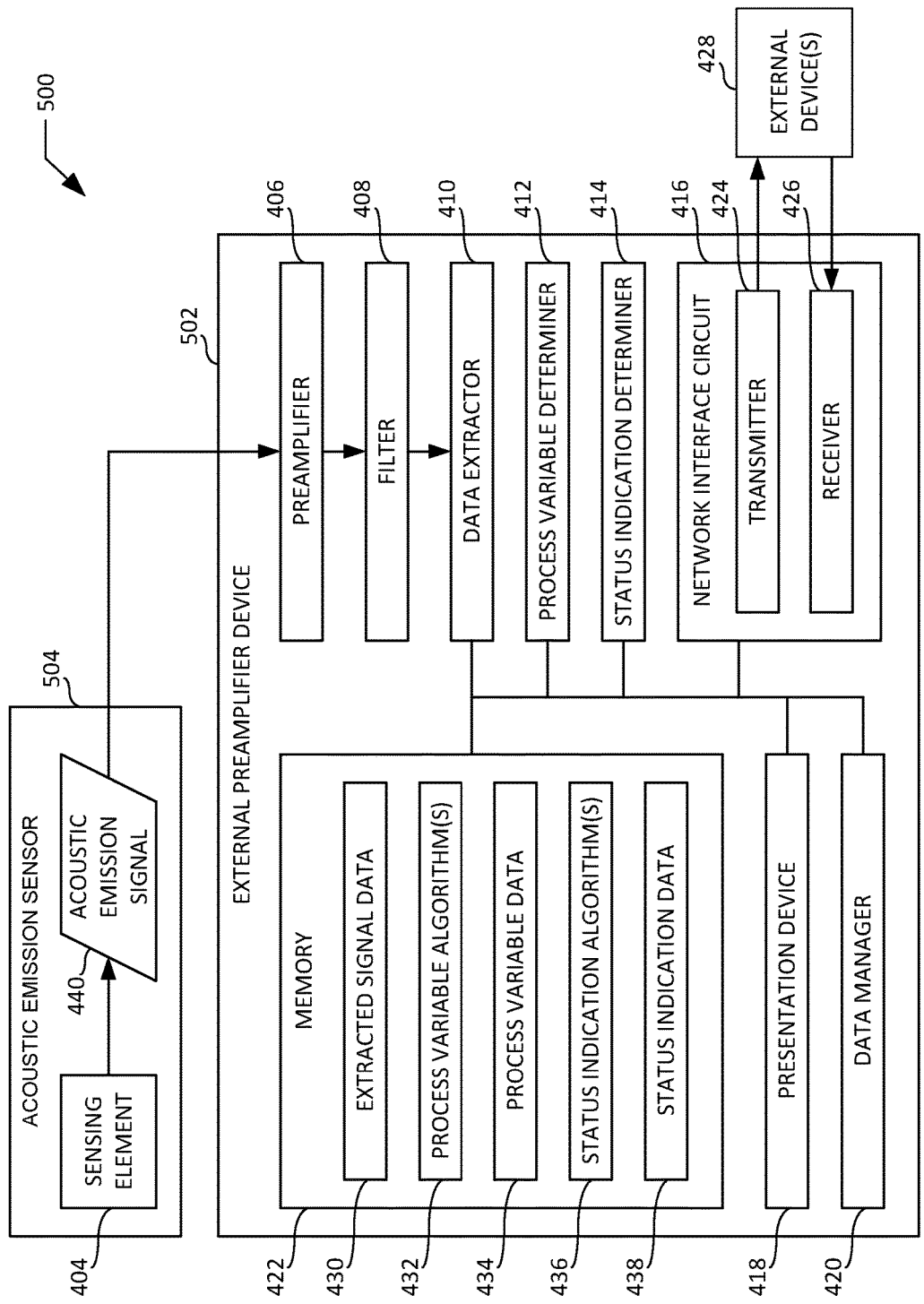
FIG. 5 is a block diagram of a second example integrated acoustic emission transducer implemented via an example external preamplifier device constructed in accordance with the teachings of this disclosure.

FIG. 5 is a block diagram of a second example integrated acoustic emission transducer 500 implemented via an example external preamplifier device 502 constructed in accordance with the teachings of this disclosure. In the illustrated example of FIG. 5, the external preamplifier device 502 is operatively coupled (e.g., in electrical communication with) an example acoustic emission sensor 504. The acoustic emission sensor 504 of FIG. 5 includes the sensing element 404 of the acoustic emission sensor 402 of FIG. 4 described above. With the exception of the sensing element 404 of FIG. 4 included within the acoustic emission sensor 504 of FIG. 5, the external preamplifier device 502 of FIG. 5 includes all of the other components, structures and data of the acoustic emission sensor 402 illustrated in FIG. 4 and described above. For example, as shown in FIG. 5, the external preamplifier device 502 includes the preamplifier 406, the filter 408, the data extractor 410, the process variable determiner 412, the status indication determiner 414, the network interface circuit 416 (including the transmitter 424 and the receiver 426), the presentation device 418, the data manager 420, and the memory 422 (including the extracted signal data 430, the one or more process variable algorithm(s) 432, the process variable data 434, the one or more status indication algorithm(s) 436, and the status indication data 438) of the acoustic emission sensor 402 of FIG. 4 described above.

In connection with the illustrated example of FIG. 5, the structure, function and/or operation of each of the preamplifier 406, the filter 408, the data extractor 410, the process variable determiner 412, the status indication determiner 414, the network interface circuit 416 (including the transmitter 424 and the receiver 426), the presentation device 418, the data manager 420, and the memory 422 (including the extracted signal data 430, the one or more process variable algorithm(s) 432, the process variable data 434, the one or more status indication algorithm(s) 436, and the status indication data 438) of the external preamplifier device 502 of FIG. 5 is/are the same as the corresponding structure, function and/or operation of the preamplifier 406, the filter 408, the data extractor 410, the process variable determiner 412, the status indication determiner 414, the network interface circuit 416 (including the transmitter 424 and the receiver 426), the presentation device 418, the data manager 420, and the memory 422 (including the extracted signal data 430, the one or more process variable algorithm(s) 432, the process variable data 434, the one or more status indication algorithm(s) 436, and the status indication data 438) of the acoustic emission sensor 402 of FIG. 4 described above. Thus, in the interest of brevity, the structure, function and/or operation of these components, structures and data of the external preamplifier device 502 of FIG. 5 are not repeated herein.

In the illustrated example of FIG. 5, the preamplifier 406, the filter 408, the data extractor 410, the process variable determiner 412, the status indication determiner 414, the network interface circuit 416, the presentation device 418, the data manager 420, and the memory 422 are integrated within the external preamplifier device 502 of the integrated acoustic emission transducer 500. In other examples, one or more of the filter 408, the data extractor 410, the process variable determiner 412, the status indication determiner 414, the network interface circuit 416, the presentation device 418, the data manager 420, and/or the memory 422 may be integrated within the preamplifier 406 of the external preamplifier device 502 of FIG. 5.

While an example manner of implementing the integrated acoustic emission transducer 500 is illustrated in FIG. 5, one or more of the elements, processes and/or devices illustrated in FIG. 5 may be combined, divided, re-arranged, omitted, eliminated and/or implemented in any other way. Further, the example preamplifier 406, the example filter 408, the example data extractor 410, the example process variable determiner 412, the example status indication determiner 414, the example network interface circuit 416, the example presentation device 418, the example data manager 420, the example memory 422 and/or, more generally the example external preamplifier device 502 of the integrated acoustic emission transducer 500 of FIG. 5 may be implemented by hardware, software, firmware and/or any combination of hardware, software and/or firmware. Thus, for example, any of the example preamplifier 406, the example filter 408, the example data extractor 410, the example process variable determiner 412, the example status indication determiner 414, the example network interface circuit 416, the example presentation device 418, the example data manager 420, the example memory 422 and/or, more generally the example external preamplifier device 502 of the integrated acoustic emission transducer 500 of FIG. 5 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example preamplifier 406, the example filter 408, the example data extractor 410, the example process variable determiner 412, the example status indication determiner 414, the example network interface circuit 416, the example presentation device 418, the example data manager 420, the example memory 422 and/or, more generally the example external preamplifier device 502 of the integrated acoustic emission transducer 500 of FIG. 5 is/are hereby expressly defined to include a non-transitory computer readable storage device or storage disk such as a memory, a digital versatile disk (DVD), a compact disk (CD), a Blu-ray disk, etc. including the software and/or firmware. Further still, the example integrated acoustic emission transducer 500 of FIG. 5 may include one or more elements, processes and/or devices in addition to, or instead of, those illustrated in FIG. 5, and/or may include more than one of any or all of the illustrated elements, processes and devices.

Figure 6:
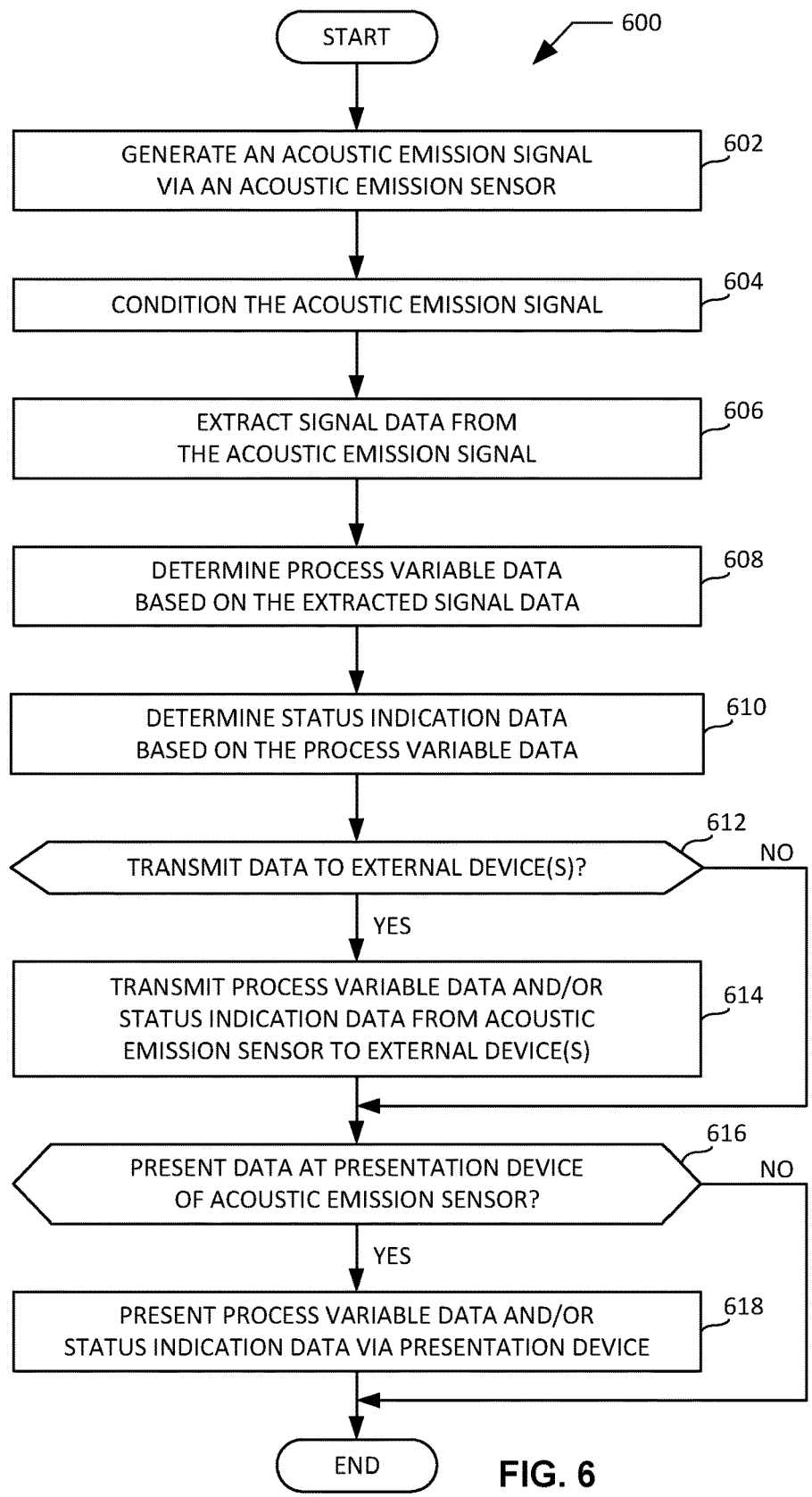
FIG. 6 is a flowchart representative of an example method for determining, transmitting, and/or presenting process variable data and/or status indication data via the first example integrated acoustic emission transducer of FIG. 4.
Figure 7:
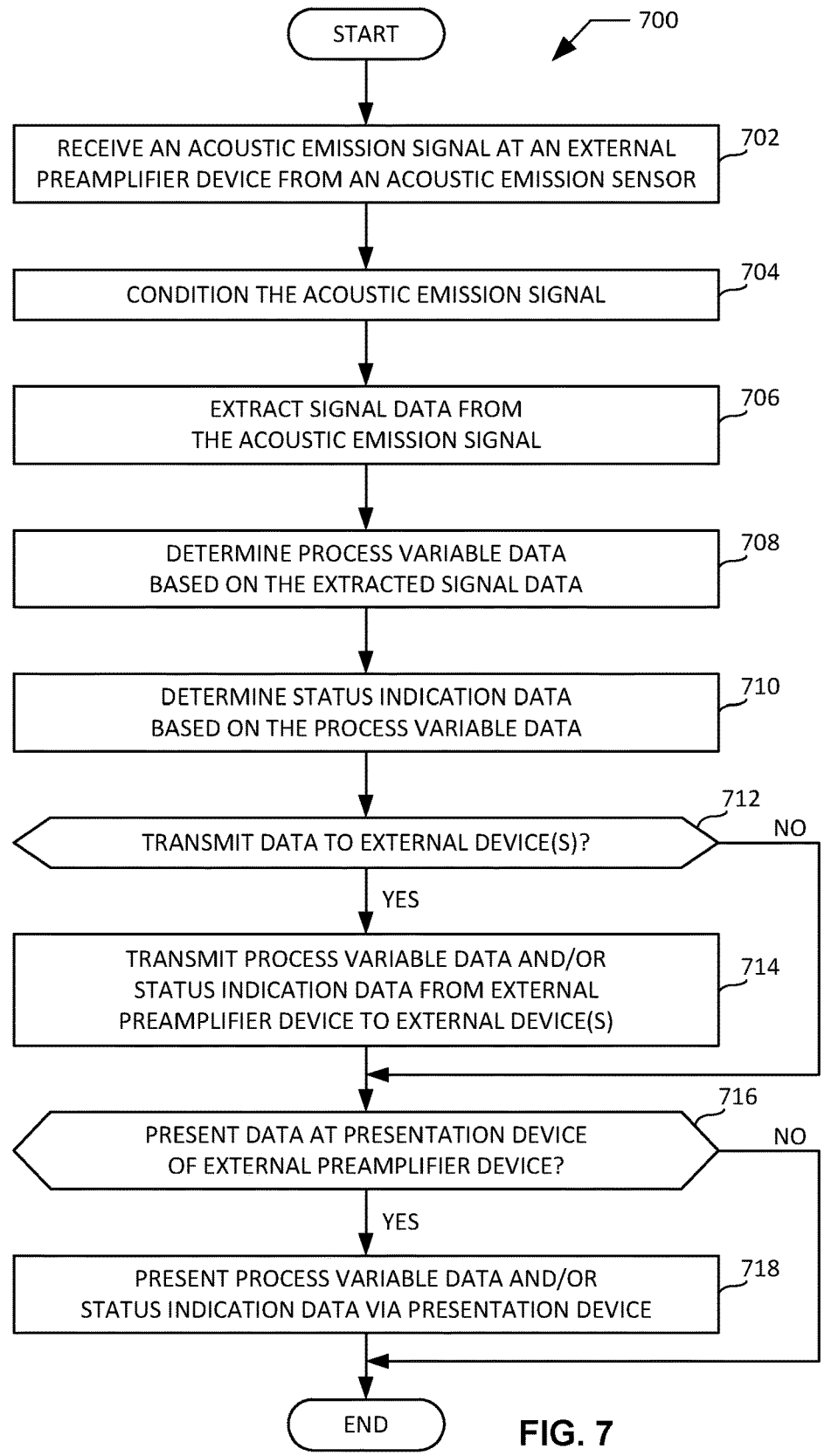
FIG. 7 is a flowchart representative of an example method for determining, transmitting, and/or presenting process variable data and/or status indication data via the second example integrated acoustic emission transducer of FIG. 5.

Flowcharts representative of example methods for determining, transmitting, and/or presenting process variable data and/or status indication data via the first example integrated acoustic emission transducer 400 of FIG. 4 and the second example integrated acoustic emission transducer 500 of FIG. 5 are respectively shown in FIGS. 6 and 7. In these examples, the methods may be implemented using machine readable instructions that comprise one or more program(s) for execution by one or more processor(s) such as the processor 802 shown in the example processor platform 800 discussed below in connection with FIG. 8, or the processor 902 shown in the example processor platform 900 discussed below in connection with FIG. 9. The one or more program(s) may be embodied in software stored on a non-transitory computer readable storage medium such as a CD-ROM, a floppy disk, a hard drive, a digital versatile disk (DVD), a Blu-ray disk, or a memory associated with the processor 802 or the processor 902, but the entirety of any program and/or parts thereof could alternatively be executed by a device other than the processor 802 or the processor 902, and/or embodied in firmware or dedicated hardware. Further, although the example program(s) is/are described with reference to the flowcharts illustrated in FIGS. 6 and 7, many other methods of implementing the first example integrated acoustic emission transducer 400 of FIG. 4 and/or the second example integrated acoustic emission transducer 500 of FIG. 5 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example methods of FIGS. 6 and 7 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. may be present without falling outside the scope of the corresponding claim. As used herein, when the phrase "at least" is used as the transition term in a preamble of a claim, it is open-ended in the same manner as the term "comprising" and "including" are open ended.

FIG. 6 is a flowchart representative of an example method 600 for determining, transmitting, and/or presenting process variable data and/or status indication data via the first example integrated acoustic emission transducer 400 of FIG. 4. The example method 600 of FIG. 6 begins when an acoustic emission sensor generates an acoustic emission signal (block 602). For example, the acoustic emission sensor 402 of FIG. 4 may generate the acoustic emission signal 440 of FIG. 4 in response to one or more acoustic emission(s) (e.g., transient elastic waves) sensed, measured and/or detected via the sensing element 404 of the acoustic emission sensor 402 of FIG. 4. Following block 602, control of the example method 600 of FIG. 6 proceeds to block 604.

At block 604, signal conditioning circuitry of the acoustic emission sensor conditions the acoustic emission signal (block 604). For example, the preamplifier 406 and/or the filter 408 of the acoustic emission sensor 402 of FIG. 4 may condition the acoustic emission signal 440 of FIG. 4 by respectively amplifying and/or filtering the acoustic emission signal 440. Following block 604, control of the example method 600 of FIG. 6 proceeds to block 606.

At block 606, a data extractor of the acoustic emission sensor extracts signal data from the acoustic emission signal (block 606). For example, the data extractor 410 of FIG. 4 may extract and/or calculate root mean square data from the acoustic emission signal 440 of FIG. 4 (e.g., as conditioned by the conditioning circuitry of the acoustic emission sensor 402 of FIG. 4 at block 604 described above) by squaring the values of the acoustic emission signal 440 (e.g., squaring the function that defines the waveform of the acoustic emission signal 440), by taking the average of the squared values (e.g., the average of the squared function), and by taking the square root of the average values (e.g., the square root of the average function). As another example, the data extractor 410 of FIG. 4 may additionally or alternatively extract and/or calculate average signal level data from the acoustic emission signal 440 of FIG. 4 by taking the average signal values (e.g., the average of the function that defines the waveform of the acoustic emission signal 440) as a function of time. In still other examples, the data extractor 410 of FIG. 4 may additionally or alternatively extract spectral content data associated with the acoustic emission signal 440 of FIG. 4, and/or transient data associated with the acoustic emission signal 440 of FIG. 4. Following block 606, control of the example method 600 of FIG. 6 proceeds to block 608.

At block 608, a process variable determiner of the acoustic emission sensor determines process variable data associated with the acoustic emission signal based on the extracted signal data (block 608). For example, the process variable determiner 412 of the acoustic emission sensor 402 of FIG. 4 may implement one or more of the process variable algorithm(s) 432 of FIG. 4 to determine the process variable data 434 of FIG. 4 based on the extracted signal data 430 of FIG. 4. In some examples, based on the extracted signal data 430 of FIG. 4 and one or more of the process variable algorithm(s) 432 of FIG. 4, the process variable determiner 412 of FIG. 4 may determine and/or calculate leakage rate data (e.g., one type of the process variable data 434 of FIG. 4) associated with a process (e.g., a flow of fluid) occurring within process equipment (e.g., process piping, a valve, etc.) being monitored via the acoustic emissions sensor 402 of FIG. 4. In other examples, again based on the extracted signal data 430 and one or more of the process variable algorithm(s) 432, the process variable determiner 412 may additionally or alternatively determine and/or calculate other types of process variable data associated with the process occurring within the process equipment. For example, the process variable data 434 of FIG. 4 determined and/or calculated by the process variable determiner 412 of FIG. 4 may additionally or alternatively include flow rate data, flow capacity data, flow area data, flow velocity data, mass accumulation data, and/or volume accumulation data associated with the process occurring within the process equipment being monitored by the acoustic emission sensor 402 of FIG. 4. Following block 608, control of the example method 600 of FIG. 6 proceeds to block 610.

At block 610, a status indication determiner of the acoustic emission sensor determines status indication data associated with the acoustic emission signal based on the determined process variable data (block 610). For example, the status indication determiner 414 of the acoustic emission sensor 402 of FIG. 4 may implement one or more of the status indication algorithm(s) 436 of FIG. 4 to determine the status indication data 438 of FIG. 4 based on the process variable data 434 of FIG. 4. In some examples, based on the process variable data 434 of FIG. 4 and one or more of the status indication algorithm(s) 436 of FIG. 4, the status indication determiner 414 of FIG. 4 may determine and/or calculate valve health data (e.g., one type of the status indication data 438 of FIG. 4) associated with process equipment (e.g., process piping, a valve, etc.) and/or a process (e.g., a flow of fluid) occurring within the process equipment, as monitored via the acoustic emissions sensor 402 of FIG. 4. In some examples, the valve health data may be expressed and/or represented as a percentage type of status indication associated with a total possible valve health (e.g., a textual, graphical and/or audible signal and/or message indicating that the valve health is eighty percent (80%) of a total possible valve health). In other examples, the valve health data may be expressed and/or represented as a pass/fail type of status indication (e.g., a textual, graphical and/or audible signal and/or message indicating that the valve health satisfies (e.g., passes) a valve health threshold or does not satisfy (e.g., fails) the valve health threshold). In other examples, again based on the process variable data 434 of FIG. 4 and one or more of the status indication algorithm(s) 436 of FIG. 4, the status indication determiner 414 of FIG. 4 may additionally or alternatively determine and/or calculate other types of status indication data associated with the process equipment and/or the process occurring within the process equipment. For example, the status indication data 438 determined and/or calculated by the status indication determiner 414 may additionally or alternatively include valve wear data, seal health data, seal wear data, and/or fugitive emissions data associated with the process equipment and/or the process occurring within the process equipment, as monitored by the acoustic emission sensor 402 of FIG. 4. In such other examples, the different types of status indication data may be expressed and/or represented in any form, including those forms described above in relation to the valve heath data. Following block 610, control of the example method 600 of FIG. 6 proceeds to block 612.

At block 612, a data manager of the acoustic emission sensor determines whether to transmit data from the acoustic emission sensor to one or more external device(s) (block 612). For example, the data manager 420 of the acoustic emission sensor 402 of FIG. 4 may determine that the process variable data 434 and/or the status indication data 438 of FIG. 4 is/are to be transmitted to one or more of the external device(s) 428 of FIG. 4. If the data manager 420 determines at block 612 that data is to be transmitted from the acoustic emission sensor 402 to one or more of the external device(s) 428, control of the example method 600 of FIG. 6 proceeds to block 614. If the data manager 420 instead determines at block 612 that data is not to be transmitted from the acoustic emission sensor 402 to one or more of the external device(s) 428, control of the example method 600 of FIG. 6 proceeds to block 616.

At block 614, a transmitter of the acoustic emission sensor transmits process variable data and/or status indication data from the acoustic emission sensor to one or more external device(s) (block 614). For example, the transmitter 424 of the acoustic emission sensor 402 of FIG. 4 may transmit the process variable data 434 and/or the status indication data 438 of FIG. 4 to one or more of the external device(s) 428 of FIG. 4. Following block 614, control of the example method 600 of FIG. 6 proceeds to block 616.

At block 616, the data manager of the acoustic emission sensor determines whether to present data at a presentation device of the acoustic emission sensor (block 616). For example, the data manager 420 of the acoustic emission sensor 402 of FIG. 4 may determine that the process variable data 434 and/or the status indication data 438 of FIG. 4 is/are to be presented at the presentation device 418 of the acoustic emission sensor 402 of FIG. 4. If the data manager 420 determines at block 616 that data is to be presented at the presentation device 418 of the acoustic emission sensor 402, control of the example method 600 of FIG. 6 proceeds to block 618. If the data manager 420 instead determines at block 616 that data is not to be presented at the presentation device 418 of the acoustic emission sensor 402, the example method 600 of FIG. 6 ends.

At block 618, the presentation device of the acoustic emission sensor presents process variable data and/or status indication data (block 618). For example, the presentation device 418 of the acoustic emission sensor 402 of FIG. 4 may present the process variable data 434 and/or the status indication data 438 of FIG. 4. Following block 618, the example method 600 of FIG. 6 ends.

FIG. 7 is a flowchart representative of an example method 700 for determining, transmitting, and/or presenting process variable data and/or status indication data via the second example integrated acoustic emission transducer 500 of FIG. 5. The example method 700 of FIG. 7 begins when an external preamplifier device receives an acoustic emission signal from an acoustic emission sensor (block 702). For example, the external preamplifier device 502 of FIG. 5 may receive the acoustic emission signal 440 of FIG. 5 from the acoustic emission sensor 504 of FIG. 5. In some examples, the acoustic emission sensor 504 of FIG. 5 may have generated the acoustic emission signal 440 of FIG. 5 in response to one or more acoustic emission(s) (e.g., transient elastic waves) sensed, measured and/or detected via the sensing element 404 of the acoustic emission sensor 504 of FIG. 5. Following block 702, control of the example method 700 of FIG. 7 proceeds to block 704.

At block 704, signal conditioning circuitry of the external preamplifier device conditions the acoustic emission signal (block 704). For example, the preamplifier 406 and/or the filter 408 of the external preamplifier device 502 of FIG. 5 may condition the acoustic emission signal 440 of FIG. 5 by respectively amplifying and/or filtering the acoustic emission signal 440. Following block 704, control of the example method 700 of FIG. 7 proceeds to block 706.

At block 706, a data extractor of the external preamplifier device extracts signal data from the acoustic emission signal (block 706). For example, the data extractor 410 of FIG. 5 may extract and/or calculate root mean square data from the acoustic emission signal 440 of FIG. 5 (e.g., as conditioned by the conditioning circuitry of the external preamplifier device 502 of FIG. 5 at block 704 described above) by squaring the values of the acoustic emission signal 440 (e.g., squaring the function that defines the waveform of the acoustic emission signal 440), by taking the average of the squared values (e.g., the average of the squared function), and by taking the square root of the average values (e.g., the square root of the average function). As another example, the data extractor 410 of FIG. 4 may additionally or alternatively extract and/or calculate average signal level data from the acoustic emission signal 440 of FIG. 4 by taking the average signal values (e.g., the average of the function that defines the waveform of the acoustic emission signal 440) as a function of time. In still other examples, the data extractor 410 of FIG. 4 may additionally or alternatively extract spectral content data associated with the acoustic emission signal 440 of FIG. 5, and/or transient data associated with the acoustic emission signal 440 of FIG. 5. Following block 706, control of the example method 700 of FIG. 7 proceeds to block 708.

At block 708, a process variable determiner of the external preamplifier device determines process variable data associated with the acoustic emission signal based on the extracted signal data (block 708). For example, the process variable determiner 412 of the external preamplifier device 502 of FIG. 5 may implement one or more of the process variable algorithm(s) 432 of FIG. 5 to determine the process variable data 434 of FIG. 5 based on the extracted signal data 430 of FIG. 5. In some examples, based on the extracted signal data 430 of FIG. 5 and one or more of the process variable algorithm(s) 432 of FIG. 5, the process variable determiner 412 of FIG. 5 may determine and/or calculate leakage rate data (e.g., one type of the process variable data 434 of FIG. 5) associated with a process (e.g., a flow of fluid) occurring within process equipment (e.g., process piping, a valve, etc.) being monitored via the acoustic emissions sensor 504 of FIG. 5. In other examples, again based on the extracted signal data 430 and one or more of the process variable algorithm(s) 432, the process variable determiner 412 may additionally or alternatively determine and/or calculate other types of process variable data associated with the process occurring within the process equipment. For example, the process variable data 434 of FIG. 5 determined and/or calculated by the process variable determiner 412 of FIG. 5 may additionally or alternatively include flow rate data, flow capacity data, flow area data, flow velocity data, mass accumulation data, and/or volume accumulation data associated with the process occurring within the process equipment being monitored by the acoustic emission sensor 504 of FIG. 5. Following block 708, control of the example method 700 of FIG. 7 proceeds to block 710.

At block 710, a status indication determiner of the external preamplifier device determines status indication data associated with the acoustic emission signal based on the determined process variable data (block 710). For example, the status indication determiner 414 of the external preamplifier device 502 of FIG. 5 may implement one or more of the status indication algorithm(s) 436 of FIG. 5 to determine the status indication data 438 of FIG. 5 based on the process variable data 434 of FIG. 5. In some examples, based on the process variable data 434 of FIG. 5 and one or more of the status indication algorithm(s) 436 of FIG. 5, the status indication determiner 414 of FIG. 5 may determine and/or calculate valve health data (e.g., one type of the status indication data 438 of FIG. 5) associated with process equipment (e.g., process piping, a valve, etc.) and/or a process (e.g., a flow of fluid) occurring within the process equipment, as monitored via the acoustic emissions sensor 504 of FIG. 5. In some examples, the valve health data may be expressed and/or represented as a percentage type of status indication associated with a total possible valve health (e.g., a textual, graphical and/or audible signal and/or message indicating that the valve health is eighty percent (80%) of a total possible valve health). In other examples, the valve health data may be expressed and/or represented as a pass/fail type of status indication (e.g., a textual, graphical and/or audible signal and/or message indicating that the valve health satisfies (e.g., passes) a valve health threshold or does not satisfy (e.g., fails) the valve health threshold). In other examples, again based on the process variable data 434 of FIG. 5 and one or more of the status indication algorithm(s) 436 of FIG. 5, the status indication determiner 414 of FIG. 5 may additionally or alternatively determine and/or calculate other types of status indication data associated with the process equipment and/or the process occurring within the process equipment. For example, the status indication data 438 determined and/or calculated by the status indication determiner 414 may additionally or alternatively include valve wear data, seal health data, seal wear data, and/or fugitive emissions data associated with the process equipment and/or the process occurring within the process equipment, as monitored by the acoustic emission sensor 504 of FIG. 5. In such other examples, the different types of status indication data may be expressed and/or represented in any form, including those forms described above in relation to the valve heath data. Following block 710, control of the example method 700 of FIG. 7 proceeds to block 712.

At block 712, a data manager of the external preamplifier device determines whether to transmit data from the external preamplifier device to one or more external device(s) (block 712). For example, the data manager 420 of the external preamplifier device 502 of FIG. 5 may determine that the process variable data 434 and/or the status indication data 438 of FIG. 5 is/are to be transmitted to one or more of the external device(s) 428 of FIG. 5. If the data manager 420 determines at block 712 that data is to be transmitted from the external preamplifier device 502 to one or more of the external device(s) 428, control of the example method 700 of FIG. 7 proceeds to block 714. If the data manager 420 instead determines at block 712 that data is not to be transmitted from the external preamplifier device 502 to one or more of the external device(s) 428, control of the example method 700 of FIG. 7 proceeds to block 716.

At block 714, a transmitter of the external preamplifier device transmits process variable data and/or status indication data from the external preamplifier device to one or more external device(s) (block 714). For example, the transmitter 424 of the external preamplifier device 502 of FIG. 5 may transmit the process variable data 434 and/or the status indication data 438 of FIG. 4 to one or more of the external device(s) 428 of FIG. 5. Following block 714, control of the example method 700 of FIG. 7 proceeds to block 716.

At block 716, the data manager of the external preamplifier device determines whether to present data at a presentation device of the external preamplifier device (block 716). For example, the data manager 420 of the external preamplifier device 502 of FIG. 5 may determine that the process variable data 434 and/or the status indication data 438 of FIG. 5 is/are to be presented at the presentation device 418 of the external preamplifier device 502 of FIG. 5. If the data manager 420 determines at block 716 that data is to be presented at the presentation device 418 of the external preamplifier device 502, control of the example method 700 of FIG. 7 proceeds to block 718. If the data manager 420 instead determines at block 716 that data is not to be presented at the presentation device 418 of the external preamplifier device 502, the example method 700 of FIG. 7 ends.

At block 718, the presentation device of the external preamplifier device presents process variable data and/or status indication data (block 718). For example, the presentation device 418 of the external preamplifier device 502 of FIG. 5 may present the process variable data 434 and/or the status indication data 438 of FIG. 5. Following block 718, the example method 700 of FIG. 7 ends.

Figure 8:
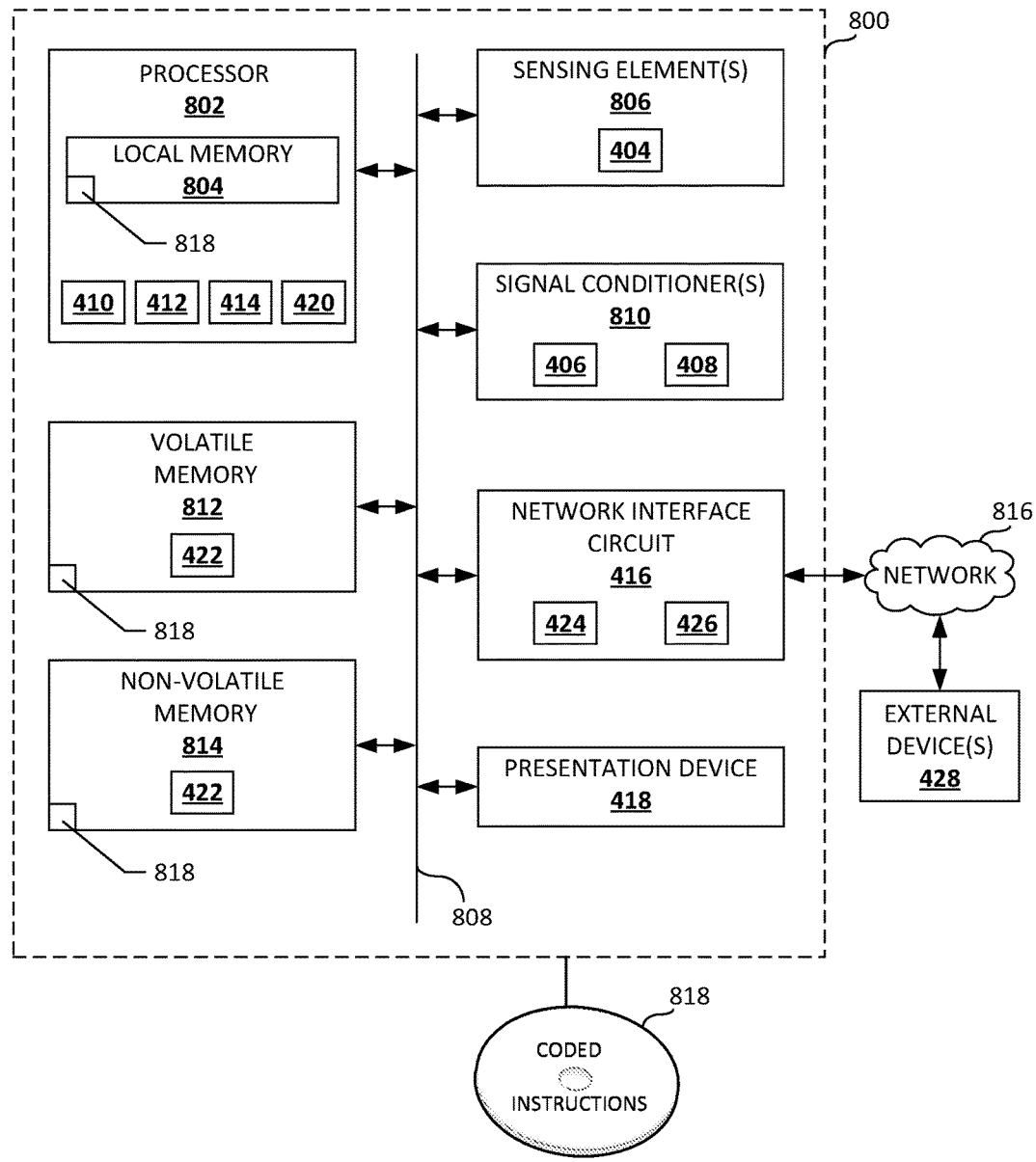
FIG. 8 is a block diagram of an example processor platform capable of executing instructions to implement the example method of FIG. 6 and the first example integrated acoustic emission transducer of FIG. 4.

FIG. 8 is a block diagram of an example processor platform 800 capable of executing instructions to implement the example method 600 of FIG. 6 and the first example integrated acoustic emission transducer 400 of FIG. 4. The processor platform 800 of the illustrated example includes a processor 802. The processor 802 of the illustrated example is hardware. For example, the processor 802 can be implemented by one or more integrated circuit(s), logic circuit(s), microprocessor(s) or controller(s) from any desired family or manufacturer. In the example of FIG. 8, the processor 802 implements the example data extractor 410, the example process variable determiner 412, the example status indication determiner 414, and the example data manager 420 of FIG. 4. The processor 802 of the illustrated example also includes a local memory 804 (e.g., a cache).

The processor 802 of the illustrated example is in communication with one or more sensing element(s) 806 via a bus 808. In the example of FIG. 8, the sensing element(s) 806 include the example sensing element 404 of FIG. 4. The processor 802 of the illustrated example is also in communication with one or more signal conditioner(s) 810 via the bus 808. In the example of FIG. 8, the signal conditioner(s) 810 include the example preamplifier 406 and the example filter 408 of FIG. 4. The processor 802 of the illustrated example is also in communication with the example presentation device 418 of FIG. 4.

The processor 802 of the illustrated example is also in communication with a main memory including a volatile memory 812 and a non-volatile memory 814 via the bus 808. The volatile memory 812 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 814 may be implemented by flash memory and/or any other desired type of memory device. Access to the volatile memory 812 and the non-volatile memory 814 is controlled by a memory controller. In the illustrated example, the main memory 812, 814 includes the example memory 422 of FIG. 4.

The processor platform 800 of the illustrated example also includes the example network interface circuit 416 of FIG. 4. The network interface circuit 416 may be implemented by any type of interface standard, such as an Ethernet interface, a universal serial bus (USB), and/or a PCI express interface. The network interface circuit 416 of the illustrated example includes the example transmitter 424 and the example receiver 426 of FIG. 4, and may further include a modem and/or a network interface card to facilitate exchange of data with the example external device(s) 428 of FIG. 4 via a network 816. In some examples, the network 816 may be facilitated via 4-20 milliamp wiring and/or via one or more communication protocol(s) including, for example, HART, Foundation Fieldbus, TCP/IP, Profinet, Modbus and/or Ethernet.

Coded instructions 818 for implementing the example method 600 of FIG. 6 may be stored in the local memory 804, in the volatile memory 812, in the non-volatile memory 814, and/or on a removable tangible computer readable storage medium such as a CD or DVD.

Figure 9:
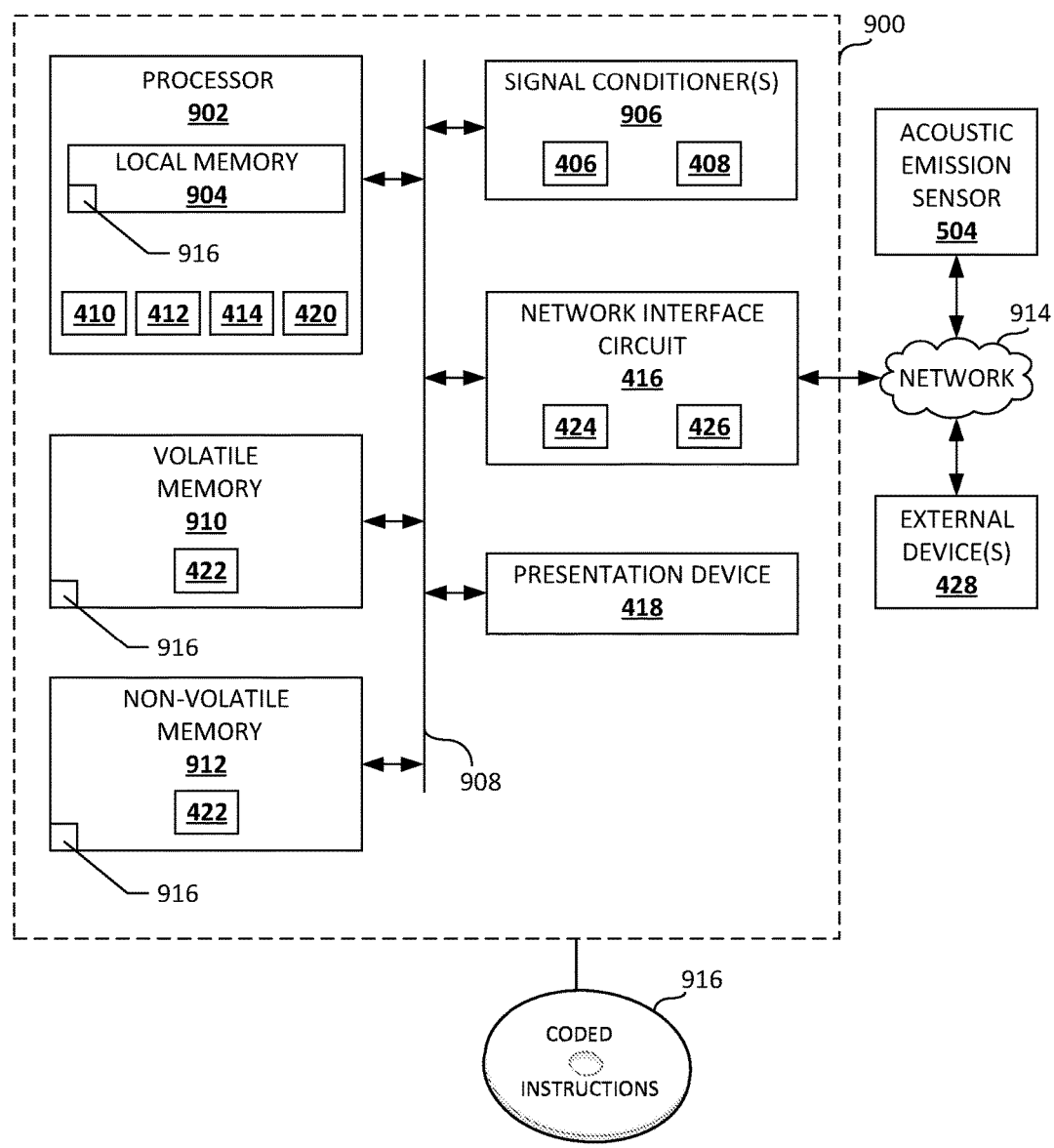
FIG. 9 is a block diagram of an example processor platform capable of executing instructions to implement the example method of FIG. 7 and the second example integrated acoustic emission transducer of FIG. 5.

FIG. 9 is a block diagram of an example processor platform 900 capable of executing instructions to implement the example method 700 of FIG. 7 and the second example integrated acoustic emission transducer 500 of FIG. 5. The processor platform 900 of the illustrated example includes a processor 902. The processor 902 of the illustrated example is hardware. For example, the processor 902 can be implemented by one or more integrated circuit(s), logic circuit(s), microprocessor(s) or controller(s) from any desired family or manufacturer. In the example of FIG. 9, the processor 902 implements the example data extractor 410, the example process variable determiner 412, the example status indication determiner 414, and the example data manager 420 of FIG. 5. The processor 902 of the illustrated example also includes a local memory 904 (e.g., a cache).

The processor 902 of the illustrated example is in communication with one or more signal conditioner(s) 906 via a bus 908. In the example of FIG. 9, the signal conditioner(s) 906 include the example preamplifier 406 and the example filter 408 of FIG. 5. The processor 902 of the illustrated example is also in communication with the example presentation device 418 of FIG. 5.

The processor 902 of the illustrated example is also in communication with a main memory including a volatile memory 910 and a non-volatile memory 912 via the bus 908. The volatile memory 910 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 912 may be implemented by flash memory and/or any other desired type of memory device. Access to the volatile memory 910 and the non-volatile memory 912 is controlled by a memory controller. In the illustrated example, the main memory 910, 912 includes the example memory 422 of FIG. 5.

The processor platform 900 of the illustrated example also includes the example network interface circuit 416 of FIG. 5. The network interface circuit 416 may be implemented by any type of interface standard, such as an Ethernet interface, a universal serial bus (USB), and/or a PCI express interface.

The network interface circuit 416 of the illustrated example includes the example transmitter 424 and the example receiver 426 of FIG. 5, and may further include a modem and/or a network interface card to facilitate exchange of data with the example external device(s) and/or the example acoustic emission sensor 504 of FIG. 5 via a network 914. In some examples, the network 914 may be facilitated via 4-20 milliamp wiring and/or via one or more communication protocol(s) including, for example, HART, Foundation Fieldbus, TCP/IP, Profinet, Modbus and/or Ethernet.

Coded instructions 916 for implementing the example method 700 of FIG. 7 may be stored in the local memory 904, in the volatile memory 910, in the non-volatile memory 912, and/or on a removable tangible computer readable storage medium such as a CD or DVD.

From the foregoing, it will be appreciated that the disclosed integrated acoustic emission transducer apparatus and methods transduce, convert, and/or restate one or more acoustic emission signal(s) generated and/or received at the integrated acoustic emission transducer into useful information (e.g., leakage rate, flow rate, valve health, valve wear, etc.) to be presented at the integrated acoustic emission transducer, and/or to be transmitted from the integrated acoustic emission transducer to an external device. Implementing the disclosed integrated acoustic emission transducer apparatus and methods advantageously enables one or more acoustic emission signal(s) generated by and/or received at the integrated acoustic emission transducer to be transduced, converted and/or restated into useful information at the integrated acoustic emission transducer in real time without the need for implementing high speed sampling and/or extensive, time-delayed, post-processing of the acoustic emission signal(s) via costly external data acquisition devices and/or external data processing devices.

In some disclosed examples, an apparatus comprises an acoustic emission sensor including a data extractor and a process variable determiner. In some disclosed examples, the acoustic emission sensor is to generate an acoustic emission signal. In some disclosed examples, the data extractor is to extract signal data from the acoustic emission signal. In some disclosed examples, the process variable determiner is to determine process variable data based on the extracted signal data. In some disclosed examples, the process variable data includes at least one of leakage rate data, flow rate data, flow capacity data, flow area data, flow velocity data, mass accumulation data, or volume accumulation data.

In some disclosed examples of the apparatus, the extracted signal data includes at least one of root mean square data associated with the acoustic emission signal, average signal level data associated with the acoustic emission signal, spectral content data associated with the acoustic emission signal, or transient data associated with the acoustic emission signal.

In some disclosed examples of the apparatus, the acoustic emission sensor further includes a status indication determiner to determine status indication data based on the process variable data. In some disclosed examples, the status indication data includes at least one of valve health data, valve wear data, seal health data, seal wear data, or fugitive emissions data. In some disclosed examples of the apparatus, the acoustic emission sensor further includes a transmitter to transmit at least one of the process variable data or the status indication data from the acoustic emission sensor to an external device. In some disclosed examples of the apparatus, the acoustic emission sensor further includes a presentation device to present at least one of the process variable data or the status indication data at the acoustic emission sensor.

In some disclosed examples of the apparatus, the acoustic emission sensor further includes signal conditioning circuitry to condition the acoustic emission signal. In some disclosed examples, the signal conditioning circuitry includes a preamplifier. In some disclosed examples of the apparatus, at least one of the data extractor or the process variable determiner is integrated within the preamplifier of the acoustic emission sensor.

In some disclosed examples, a method comprises extracting signal data at an acoustic emission sensor from an acoustic emission signal generated via the acoustic emission sensor. In some disclosed examples, the method further comprises determining process variable data at the acoustic emission sensor based on the extracted signal data. In some disclosed examples, the process variable data includes at least one of leakage rate data, flow rate data, flow capacity data, flow area data, flow velocity data, mass accumulation data, or volume accumulation data.

In some disclosed examples of the method, the extracted signal data includes at least one of root mean square data associated with the acoustic emission signal, average signal level data associated with the acoustic emission signal, spectral content data associated with the acoustic emission signal, or transient data associated with the acoustic emission signal.

In some disclosed examples, the method further comprises determining status indication data at the acoustic emission sensor based on the process variable data. In some disclosed examples, the status indication data includes at least one of valve health data, valve wear data, seal health data, seal wear data, or fugitive emissions data. In some disclosed examples, the method further comprises transmitting at least one of the process variable data or the status indication data from the acoustic emission sensor to an external device. In some disclosed examples, the method further comprises presenting at least one of the process variable data or the status indication data at the acoustic emission sensor via a presentation device of the acoustic emission sensor.

In some examples, a non-transitory computer readable storage medium comprising instructions is disclosed. In some disclosed examples, the instructions, when executed, cause a processor to extract signal data at an acoustic emission sensor from an acoustic emission signal generated via the acoustic emission sensor. In some disclosed examples, the instructions, when executed, further cause the processor to determine process variable data at the acoustic emission sensor based on the extracted signal data. In some disclosed examples, the process variable data includes at least one of leakage rate data, flow rate data, flow capacity data, flow area data, flow velocity data, mass accumulation data, or volume accumulation data.

In some disclosed examples of the non-transitory computer readable storage medium, the extracted signal data includes at least one of root mean square data associated with the acoustic emission signal, average signal level data associated with the acoustic emission signal, spectral content data associated with the acoustic emission signal, or transient data associated with the acoustic emission signal.

In some disclosed examples of the non-transitory computer readable storage medium, the instructions, when executed, further cause the processor to determine status indication data at the acoustic emission sensor based on the process variable data. In some disclosed examples, the status indication data includes at least one of valve health data, valve wear data, seal health data, seal wear data, or fugitive emissions data. In some disclosed examples, the instructions, when executed, further cause the processor to instruct a transmitter of the acoustic emission sensor to transmit at least one of the process variable data or the status indication data from the acoustic emission sensor to an external device. In some disclosed examples, the instructions, when executed, further cause the processor to instruct a presentation device of the acoustic emission sensor to present at least one of the process variable data or the status indication data at the acoustic emission sensor.

In some disclosed examples, an apparatus comprises an external preamplifier device including a data extractor and a process variable determiner. In some disclosed examples, the external preamplifier device is to receive an acoustic emission signal generated via an acoustic emission sensor operatively coupled to the external preamplifier device. In some disclosed examples, the data extractor is to extract signal data from the acoustic emission signal. In some disclosed examples, the process variable determiner is to determine process variable data based on the extracted signal data. In some disclosed examples, the process variable data includes at least one of leakage rate data, flow rate data, flow capacity data, flow area data, flow velocity data, mass accumulation data, or volume accumulation data.

In some disclosed examples of the apparatus, the extracted signal data includes at least one of root mean square data associated with the acoustic emission signal, average signal level data associated with the acoustic emission signal, spectral content data associated with the acoustic emission signal, or transient data associated with the acoustic emission signal.

In some disclosed examples of the apparatus, the external preamplifier device further includes a status indication determiner to determine status indication data based on the process variable data. In some disclosed examples, the status indication data includes at least one of valve health data, valve wear data, seal health data, seal wear data, or fugitive emissions data. In some disclosed examples of the apparatus, the external preamplifier device further includes a transmitter to transmit at least one of the process variable data or the status indication data from the external preamplifier device to an external device. In some disclosed examples of the apparatus, the external preamplifier device further includes a presentation device to present at least one of the process variable data or the status indication data at the external preamplifier device.

In some disclosed examples of the apparatus, the external preamplifier device further includes signal conditioning circuitry to condition the acoustic emission signal. In some disclosed examples, the signal conditioning circuitry includes a preamplifier. In some disclosed examples of the apparatus, at least one of the data extractor or the process variable determiner is integrated within the preamplifier of the external preamplifier device.

In some disclosed examples, a method comprises extracting signal data at an external preamplifier device from an acoustic emission signal received at the external preamplifier device. In some disclosed examples, the acoustic emission signal is generated via an acoustic emission sensor operatively coupled to the external preamplifier device. In some disclosed examples, the method further comprises determining process variable data at the external preamplifier device based on the extracted signal data. In some disclosed examples, the process variable data includes at least one of leakage rate data, flow rate data, flow capacity data, flow area data, flow velocity data, mass accumulation data, or volume accumulation data.

In some disclosed examples of the method, the extracted signal data includes at least one of root mean square data associated with the acoustic emission signal, average signal level data associated with the acoustic emission signal, spectral content data associated with the acoustic emission signal, or transient data associated with the acoustic emission signal.

In some disclosed examples, the method further comprises determining status indication data at the external preamplifier device based on the process variable data. In some disclosed examples, the status indication data includes at least one of valve health data, valve wear data, seal health data, seal wear data, or fugitive emissions data. In some disclosed examples, the method further comprises transmitting at least one of the process variable data or the status indication data from the external preamplifier device to an external device. In some disclosed examples, the method further comprises presenting at least one of the process variable data or the status indication data at the external preamplifier device via a presentation device of the external preamplifier device.

In some examples, a non-transitory computer readable storage medium comprising instructions is disclosed. In some disclosed examples, the instructions, when executed, cause a processor to extract signal data at an external preamplifier device from an acoustic emission signal received at the external preamplifier device. In some disclosed examples, the acoustic emission signal is generated via an acoustic emission sensor operatively coupled to the external preamplifier device. In some disclosed examples, the instructions, when executed, further cause the processor to determine process variable data at the external preamplifier device based on the extracted signal data. In some disclosed examples, the process variable data includes at least one of leakage rate data, flow rate data, flow capacity data, flow area data, flow velocity data, mass accumulation data, or volume accumulation data.

In some disclosed examples of the non-transitory computer readable storage medium, the extracted signal data includes at least one of root mean square data associated with the acoustic emission signal, average signal level data associated with the acoustic emission signal, spectral content data associated with the acoustic emission signal, or transient data associated with the acoustic emission signal.

In some disclosed examples of the non-transitory computer readable storage medium, the instructions, when executed, further cause the processor to determine status indication data at the external preamplifier device based on the process variable data. In some disclosed examples, the status indication data includes at least one of valve health data, valve wear data, seal health data, seal wear data, or fugitive emissions data. In some disclosed examples, the instructions, when executed, further cause the processor to instruct a transmitter of the external preamplifier device to transmit at least one of the process variable data or the status indication data from the external preamplifier device to an external device. In some disclosed examples, the instructions, when executed, further cause the processor to instruct a presentation device of the external preamplifier device to present at least one of the process variable data or the status indication data at the external preamplifier device.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus, comprising:
an integrated acoustic emission sensor including a data extractor, a process variable determiner, a status indication determiner, and a presentation device, the integrated acoustic emission sensor to generate an acoustic emission signal, the data extractor to extract signal data from the acoustic emission signal, the process variable determiner to determine process variable data based on the extracted signal data, the process variable data including at least one of flow rate data, flow capacity data, flow area data, flow velocity data, mass accumulation data, or volume accumulation data, the status indication determiner to determine status indication data based on the process variable data, the presentation device to present at least one of the process variable data or the status indication data at the integrated acoustic emission sensor.

2. The apparatus of claim 1, wherein the extracted signal data includes at least one of root mean square data associated with the acoustic emission signal, average signal level data associated with the acoustic emission signal, spectral content data associated with the acoustic emission signal, or transient data associated with the acoustic emission signal.

3. The apparatus of claim 1, wherein the status indication data includes at least one of valve health data, valve wear data, or fugitive emissions data.

4. The apparatus of claim 1, wherein the integrated acoustic emission sensor further includes a transmitter to transmit at least one of the process variable data or the status indication data from the integrated acoustic emission sensor to an external device.

5. The apparatus of claim 1, wherein the integrated acoustic emission sensor further includes signal conditioning circuitry to condition the acoustic emission signal, the signal conditioning circuitry including a preamplifier.

6. The apparatus of claim 5, wherein at least one of the data extractor or the process variable determiner is integrated within the preamplifier of the integrated acoustic emission sensor.

7. The apparatus of claim 1, wherein the presentation device is to present the at least one of the process variable data or the status indication data at the integrated acoustic emission sensor in real time.

8. The apparatus of claim 1, wherein the presentation device is to present the status indication data at the integrated acoustic emission sensor as a percentage type.

9. A method, comprising:
extracting signal data at an integrated acoustic emission sensor from an acoustic emission signal generated via the integrated acoustic emission sensor;
determining process variable data at the integrated acoustic emission sensor based on the extracted signal data, the process variable data including at least one of flow rate data, flow capacity data, flow area data, flow velocity data, mass accumulation data, or volume accumulation data;
determining status indication data at the integrated acoustic emission sensor based on the process variable data; and
presenting at least one of the process variable data or the status indication data at the integrated acoustic emission sensor.

10. The method of claim 9, wherein the extracted signal data includes at least one of root mean square data associated with the acoustic emission signal, average signal level data associated with the acoustic emission signal, spectral content data associated with the acoustic emission signal, or transient data associated with the acoustic emission signal.

11. The method of claim 9, wherein the status indication data includes at least one of valve health data, valve wear data, or fugitive emissions data.

12. The method of claim 9, further comprising transmitting at least one of the process variable data or the status indication data from the integrated acoustic emission sensor to an external device.

13. The method of claim 9, wherein the presenting of the at least one of the process variable data or the status indication data at the integrated acoustic emission sensor is in real time.

14. The method of claim 9, wherein the status indication data is presented at the integrated acoustic emission sensor as a percentage type.

15. A non-transitory computer readable storage medium comprising instructions that, when executed, cause a processor to at least:
extract signal data at an integrated acoustic emission sensor from an acoustic emission signal generated via the integrated acoustic emission sensor;
determine process variable data at the integrated acoustic emission sensor based on the extracted signal data, the process variable data including at least one of flow rate data, flow capacity data, flow area data, flow velocity data, mass accumulation data, or volume accumulation data;
determine status indication data at the integrated acoustic emission sensor based on the process variable data; and
present at least one of the process variable data or the status indication data at the integrated acoustic emission sensor.

16. The non-transitory computer readable storage medium of claim 15, wherein the extracted signal data includes at least one of root mean square data associated with the acoustic emission signal, average signal level data associated with the acoustic emission signal, spectral content data associated with the acoustic emission signal, or transient data associated with the acoustic emission signal.

17. The non-transitory computer readable storage medium of claim 15, wherein the status indication data includes at least one of valve health data, valve wear data, or fugitive emissions data.

18. The non-transitory computer readable storage medium of claim 15, wherein the instructions, when executed, further cause the processor to instruct a transmitter of the integrated acoustic emission sensor to transmit at least one of the process variable data or the status indication data from the integrated acoustic emission sensor to an external device.

19. The non-transitory computer readable storage medium of claim 15, wherein the instructions, when executed, cause the processor to present the at least one of the process variable data or the status indication data at the integrated acoustic emission sensor in real time.

20. The non-transitory computer readable storage medium of claim 15, wherein the status indication data is to be presented at the integrated acoustic emission sensor as a percentage type.

* * * * *